(12) United States Patent
Robinson

(10) Patent No.: US 11,975,009 B2
(45) Date of Patent: May 7, 2024

(54) USE OF ZINC PORPHYRIN AS AN ANTIMICROBIAL

(71) Applicant: ZNABLE LLC, Northport, MI (US)

(72) Inventor: Jayne Robinson, Northport, MI (US)

(73) Assignee: ZNABLE LLC, Northport, MI (US)

( * ) Notice: Subject to any disclaimer, the term of this patent is extended or adjusted under 35 U.S.C. 154(b) by 0 days.

(21) Appl. No.: 17/734,581

(22) Filed: May 2, 2022

(65) Prior Publication Data

US 2023/0346798 A1    Nov. 2, 2023

(51) Int. Cl.
| | | |
|---|---|---|
| A61K 31/555 | (2006.01) | |
| A01N 59/16 | (2006.01) | |
| A01P 1/00 | (2006.01) | |
| A61K 45/06 | (2006.01) | |
| A61P 31/04 | (2006.01) | |

(52) U.S. Cl.
CPC ............ *A61K 31/555* (2013.01); *A01N 59/16* (2013.01); *A01P 1/00* (2021.08); *A61K 45/06* (2013.01); *A61P 31/04* (2018.01)

(58) Field of Classification Search
None
See application file for complete search history.

(56) References Cited

U.S. PATENT DOCUMENTS

| | | |
|---|---|---|
| 8,551,456 B2 | 10/2013 | Robinson et al. |
| 9,364,537 B2 | 6/2016 | Robinson et al. |

FOREIGN PATENT DOCUMENTS

WO    WO-2016028633 A2 *  2/2016  ............ A01N 43/90

OTHER PUBLICATIONS

Patel et al. "A Cationic Porphyrin, ZnPor, Disassembles Pseudomonas aeruginosa Biofilm Matrix, Kills Cells Directly, and Enhances Antibiotic Activity of Tobramycin," Antibiotics 2020, 9, 875 1-17, published Dec. 6, 2020. (Year: 2020).*
Lu et al. "Dispersing biofilms with engineered enzymatic bacteriophage," PNAS Jul. 3, 2007 vol. 104 No. 27 p. 11197-11202. (Year: 2007).*
Li et al. "A combination therapy of Phages and Antibiotics: Two is better than one," Int. J. Biol. Sci. 2021, vol. 17 published Aug. 18, 2021. (Year: 2021).*
Yoho, J., C. Stroh, S. Swavey, and M. Kango-Singh. 2014. Toxicity and localization studies of a potential photodynamic therapy agent in *Drosophila*. Genesis 52(4):309 Photochem Photobiol.
Patel N, Swavey S, Robinson J. A Cationic Porphyrin, ZnPor, Disassembles Pseudomonas aeruginosa Biofilm Matrix, Kills Cells Directly, and Enhances Antibiotic Activity of Tobramycin. Antibiotics (Basel). Dec. 6, 2020;9(12):875. doi: 10.3390/antibiotics9120875. PMID: 33291344; PMCID: PMC7762324.
Hynen AL, Lazenby JJ, Savva GM, McCaughey LC, Turnbull L, Nolan LM, Whitchurch CB. Multiple holins contribute to extracellular DNA release in Pseudomonas aeruginosa biofilms. Microbiology (Reading). Feb. 2021;167(2):000990. doi: 10.1099/mic.0.000990. PMID: 33400641; PMCID: PMC8131026.obiol. Nov. 2010;61(5):411-6. doi: 10.1007/s00284-010-9629-y. Epub Apr. 6, 2010. PMID: 20372908.
Zemanick, E.T. and L.R. Hoffman, Cystic Fibrosis: Microbiology and Host Response. Pediatr Clin North Am, 2016. 63(4): p. 617-36.
Mogayzel, P.J., Jr., et al., Cystic fibrosis pulmonary guidelines. Chronic medications for maintenance of lung health. Am J Respir Crit Care Med, 2013. 187(7): p. 680-9.
Flume, P.A., et al., Cystic fibrosis pulmonary guidelines: airway clearance therapies. Respir Care, 2009. 54(4): p. 522-37.
Davis, P.B., M. Drumm, and M.W. Konstan, Cystic fibrosis. Am J Respir Crit Care Med, 1996. 154(5): p. 1229-56.
Simon, R. Cystic fibrosis: Antibiotic therapy for chronic pulmonary infection.
Rowbotham, N.J., et al., The top 10 research priorities in cystic fibrosis developed by a partnership between people with CF and healthcare providers. Thorax, 2018.
Mogayzel, P.J., Jr., et al., Cystic Fibrosis Foundation pulmonary guideline. pharmacologic approaches to prevention and eradication of initial Pseudomonas aeruginosa infection. Ann Am Thorac Soc, 2014.
Bjarnsholt, T., et al., Pseudomonas aeruginosa biofilms in the respiratory tract of cystic fibrosis patients. Pediatr Pulmonol, 2009. 44(6): p. 547-58.
Hoiby, N., O. Ciofu, and T. Bjarnsholt, Pseudomonas aeruginosa biofilms in cystic fibrosis. Future Microbiol, 2010. 5(11): p. 1663-74.
Murray, T.S., M. Egan, and B.I. Kazmierczak, Pseudomonas aeruginosa chronic colonization in cystic fibrosis patients. Curr Opin Pediatr, 2007. 19(1): p. 83-8.
Charnyi, A.M. and S.E. Krasovitskaia, [Porphyrins]. Usp Sovrem Biol, 1951. 32(2): p. 166-92.
Falk, J.E., Porphyrins. Br Med Bull, 1954. 10(3): p. 211-4.
Huang, H., et al., Emerging applications of porphyrins in photomedicine. Frontiers in Physics, 2015. 3(23).
Huang, X., K. Nakanishi, and N. Berova, Porphyrins and metalloporphyrins: versatile circular dichroic reporter groups for structural studies. Chirality, 2000. 12(4): p. 237-55.
Fiel RJ, Howard JC, Mark EH, Datta Gupta N. Interaction of DNA with a porphyrin ligand: evidence for intercalation. Nucleic Acids Res. Jul. 11, 1979;6(9):3093-118. doi: 10.1093/nar/6.9.3093. PMID: 573891; PMCID: PMC327919.
Yoho, J. et al., Toxicity and localization studies of a potential photodynamic therapy agent in *Drosophila*, 2014.

(Continued)

*Primary Examiner* — Jeffrey S Lundgren
*Assistant Examiner* — Michael J Schmitt
(74) *Attorney, Agent, or Firm* — Aurora Consulting LLC; Ashley Sloat

(57) ABSTRACT

The present disclosure provides for a method of inhibiting the growth of a microorganism including contacting the microorganism with zinc porphyrin (ZnPor). The present disclosure also provides for a method of treating or preventing biofilm formation of one or more microorganisms including contacting the biofilm with zinc porphyrin (ZnPor). Further, the present disclosure provides for a method of treating a disease associated with biofilm formation in a subject including administering to the subject a composition comprising a therapeutically effective amount of ZnPor.

29 Claims, 18 Drawing Sheets

(56) References Cited

OTHER PUBLICATIONS

Choi, J.K., A. D'Urso, and M. Balaz, Chiroptical properties of anionic and cationic porphyrins and metalloporphyrins in complex with left-handed Z-DNA and right-handed B-DNA. J Inorg Biochem, 2013. 127: p. 1-6.
Chiang, W. C., Nilsson, M., Jensen, P. Ø., Høiby, N., Nielsen, T. E., Givskov, M., & Tolker-Nielsen, T. (2013). Extracellular DNA shields against aminoglycosides in Pseudomonas aeruginosa biofilms. Antimicrobial agents and chemotherapy, 57(5), 2352-2361.
Montanaro, L., et al., Extracellular DNA in Biofilms. The International Journal of Artificial Organs, 2011. 34(9): p. 824-831.
Okshevsky, M., V. R. Regina, and R. Meyer, Extracellular DNA as a target for biofilm control. Current Opinion in Biotechnology, 2015. 33: p. 73-80.
Munita, J.M. and C.A. Arias, Mechanisms of Antibiotic Resistance. Microbiology spectrum, 2016. 4(2): p. 10.1128/microbiolspec. VMBF-0016-2015.
Salcedo, D.E., et al., The effects of antibiotics on the biofilm formation and antibiotic resistance gene transfer. Desalination and Water Treatment, 2015. 54(13): p. 3582-3588.
Gula, G., et al., Complex Signaling Networks Controlling Dynamic Molecular Changes in Pseudomonas aeruginosa Biofilm. Curr Med Chem, 2019. 26(11): p. 1979-1993.
Vorkapic, D., K. Pressler, and S. Schild, Multifaceted roles of extracellular DNA in bacterial physiology. Curr Genet, 2016. 62(1): p. 71-9.
Collins, T.L., et al., The effect of a cationic porphyrin on Pseudomonas aeruginosa biofilms. Curr Microbiol, 2010. 61(5): p. 411-6.
Lutton, J.D., et al., Zinc porphyrins: potent inhibitors of hematopoieses in animal and human bone marrow. Proc Natl Acad Sci U S A, 1997. 94(4): p. 1432-6.
Nolan LM, Turnbull L, Katrib M, Osvath SR, Losa D, Lazenby JJ, Whitchurch CB. Pseudomonas aeruginosa is capable of natural transformation in biofilms. Microbiology (Reading). Oct. 2020;166(10):995-1003. doi: 10.1099/mic.0.000956. PMID: 32749953; PMCID: PMC7660920.
Gralinski, L. E., & Baric, R. S. (2015). Molecular pathology of emerging coronavirus infections. The Journal of pathology, 235(2), 185-195.
Cavanagh, 2005, "Coronaviridae: a review of coronavirus and toroviruses", Coronaviruses with Special Emphasis on First Insights Concerning SARS 1, ed. By A. Schmidt, M.H. Wolff and O. Weber, Birkhauser Verlag Baser, Switzerland.

\* cited by examiner

| Cell Type | Description |
|---|---|
| BEAS-2B | Human bronchial epithelial cell |
| 16HBE | Bronchial epithelial cell; high CFTR RNA/protein expression |
| CFBE | Bronchial epithelial cell, ΔF508 CFTR mutation, defective chloride transport |

| Assay | Cellular Mechanism |
|---|---|
| LDH | Cytotoxicity, cell lysis |
| TUNEL staining | DNA fragmentation |
| Annexin V-PI flow cytometry | Phosphatidylserine exposure (annexin V), cell viability (PI) |
| Measurement of caspase activity: calorimetric assay | Intrinsic: caspase-7, -9<br>Extrinsic: caspase-8<br>Executioner caspases: caspase-3 |
| Protein measurement: Western blot, IHC | Intrinsic apoptosis: BCL-2 family proteins, caspase-7 and -9, cytochrome C (cytosolic fraction)<br>Extrinsic apoptosis: FasL, TRAIL, TNF, TNFR1, TRAILR1 and -2, caspase-8<br>BCL-2 Family Members:<br>    • Anti-apoptosis: BCL-$X_L$, BCL-B, MCL-1<br>    • Pro-apoptosis: BAX, BAK, Bid, Bim<br>Common Apoptotic Pathways: PARP (total- and cleaved-), cleaved caspase-3 (total- and cleaved-) |

FIG. 8

| Assay | Mechanism |
|---|---|
| Total cell count | Cellular migration and inflammation |
| Cell differential (manual) | Presence of lymphocytes, neutrophils, eosinophils |
| Total protein | Inflammation, vascular leak |
| Lactate dehydrogenase (LDH) | Inflammation, vascular leak, cell death |
| Histopathology (HE staining) | Inflammation |

| Average Log CFU/mL | Polyethylene | | Titanium | | Hydroxyapatite | |
|---|---|---|---|---|---|---|
| | Light | Dark | Light | Dark | Light | Dark |
| Control | 9.3 ±0.1 | | 8.8 ±0.1 | | 9.0 ±0.1 | |
| ZnPor Only | 6.4 ±0.1 | | 7.6 ±0.1 | | 5.4 ±0.3 | |
| PEV2 Only | 7.8 ±0.1 | | 4.1 ±0.2 | | 7.6 ±0.1 | |
| ZnPor then PEV2 | 1.3 ±0.4 | | 3.3 ±0.2 | | 3.0 ±0.2 | |

A

| Average Log PFU/mL | Polyethylene | | Titanium | | Hydroxyapatite | |
|---|---|---|---|---|---|---|
| | Light | Dark | Light | Dark | Light | Dark |
| PEV2 Only | 7.8 ±0.7 | | 7.0± 0.5 | | 6.5 ± 0.3 | |
| ZnPor then PEV2 | 0.8 ±0.8 | | 0 | | 0 | |

B

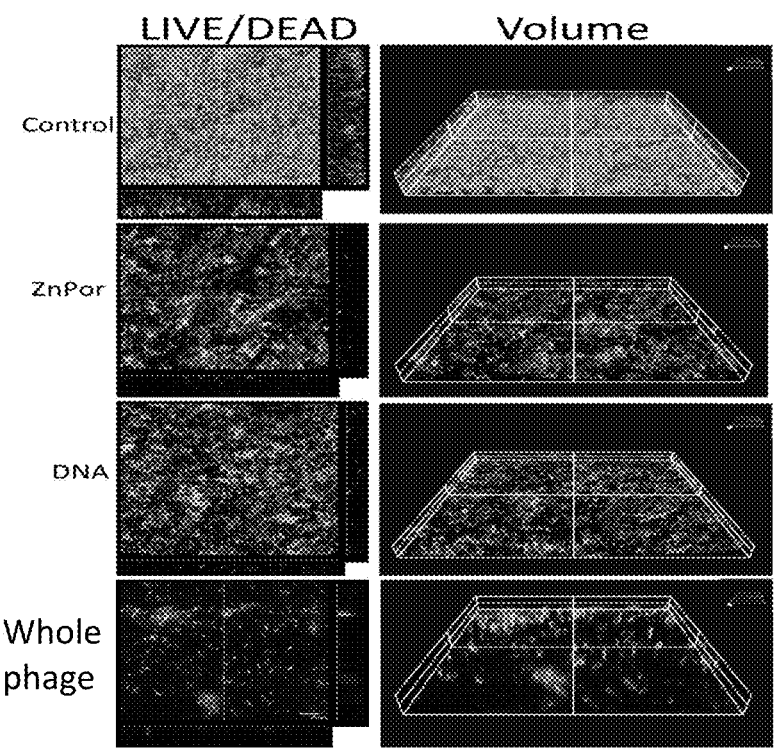
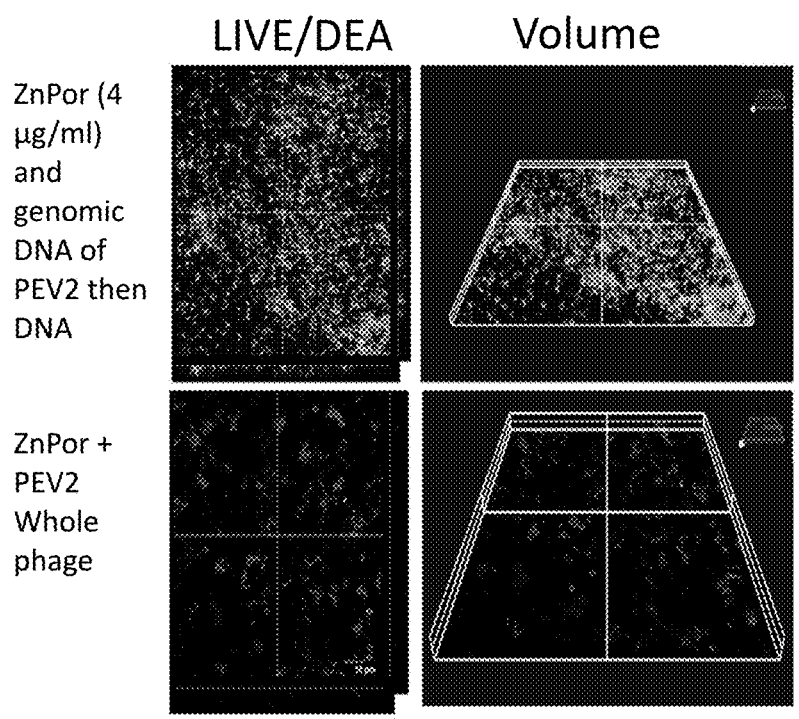
FIG. 20

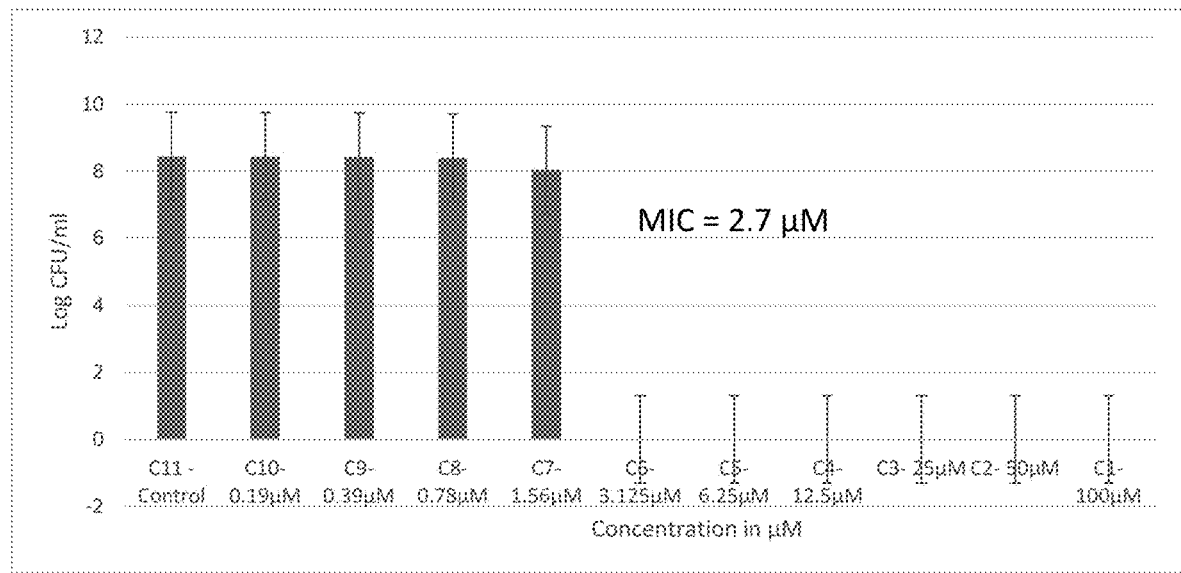
A
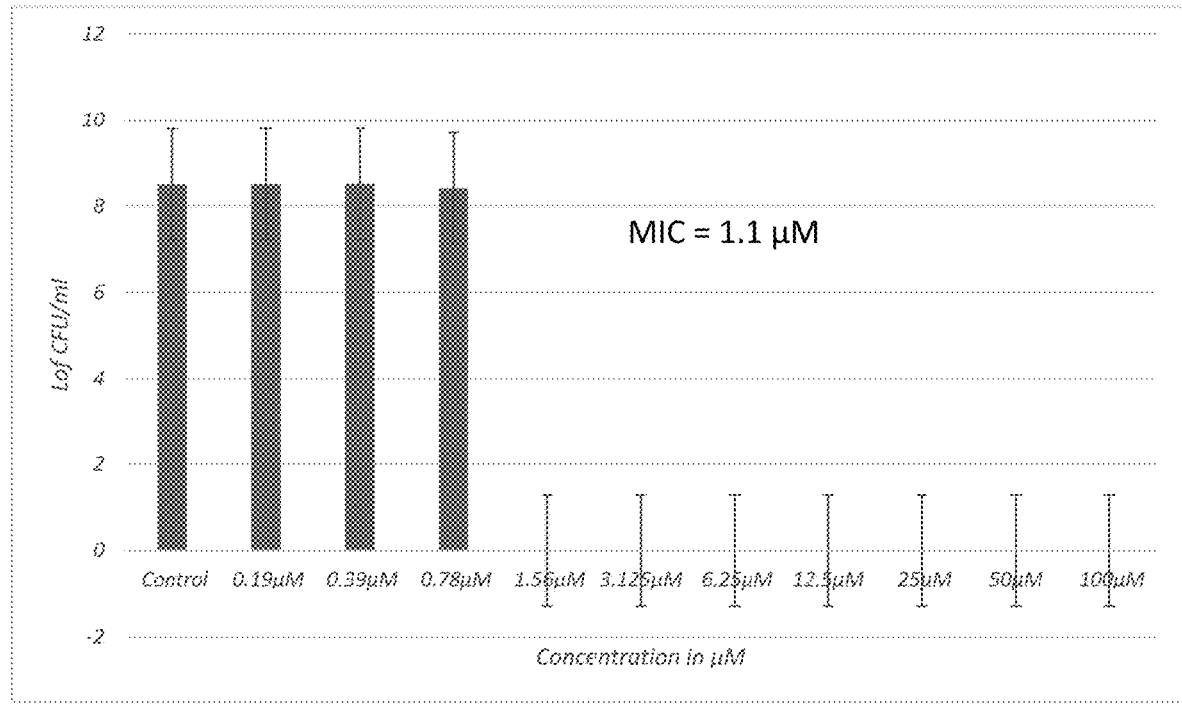
B
FIG. 26

USE OF ZINC PORPHYRIN AS AN ANTIMICROBIAL

BACKGROUND

There is a critical need for novel antimicrobials and anti-infectives to fight an increasing cadre of emerging diseases caused by microorganisms, e.g., COVID-19, as well as to treat known diseases caused by microbes that have developed resistance to one or more extant antimicrobials (e.g., the bacterium that causes TB, *Mycobacterium tuberculosis*).

Development of novel antibiotics and antimicrobials (including antivirals) has become a top priority of scientists worldwide, as microbial infection threats have grown in both virility and resistance. According to the CDC report of 2019, more than 2.8 million people acquired antibiotic resistant infections, causing more than 35,000 deaths a year. Covid-19 has killed over 850,000 people in the US, and over 5.5 million individuals worldwide. Recent reports have shown that the COVID-19 virus is developing resistance to an extant antiviral medication, which is not unheard of for viruses.

Additionally, many bacteria are now resistant to more than one antibiotic; referred to as MDR (Multiple Drug Resistance). These MDR strains of bacteria, especially bacteria that grow in biofilm mode, are considered the source of persistent infections. Bacteria that grow in biofilms are up to 1000× more resistant to antibiotics.

New technologies are needed to combat this growing threat to human health. For several decades the development of new small molecule antibiotics, (e.g., penicillin) was suspended due to a legitimate fear of the development of resistance. For example, methicillin resistance predates commercial production of the antibiotic. Development of these more complex, and costly treatments have long time horizons. And each has their own limitations—e.g., bacteria easily develop resistance to bacteriophage via CRISPR-Cas systems (as well as other mechanisms).

Phage therapy holds great promise and is being pursued in many countries, but phage therapy comes with serious limitations and safety concerns. Phage therapy involves the risk of genetic transduction of antibiotic resistance genes and inconsistent pharmacokinetics among them; demanding the use of highly characterized phage. And there are barriers to its effectiveness: (1) Phage are notorious for being able to infect only a limited cadre of bacteria—sometimes just a single strain (e.g., PEV2 phage kills PsA strain PAO1 but not PA14). (See FIGS. 13A-13B.) This specificity comes from the fact that phage must attach to receptors on the host bacterium's cell surface. Bacteria are known to develop resistance to bacteriophage using several mechanisms, making CRISPR of greatest interest at this time. though only about 50% of bacteria have a CRISPR system.

In order to study and use the powerful CRISPR-Cas system in bacteria, especially those that do not have their own system, researchers (REF) have developed a plasmid vector with the CRISPR-Cas system components that can be transferred into bacteria using artificial means, in vitro, in the laboratory, which includes electroporation or chemical treatment of the bacteria with $CaCl_2$ or $MgCl_2$ in the lab.

What is needed is a way to make bacteria permeable to the uptake of antibiotics, exogenous DNA, reagents, or even whole phage in a manner that does not require artificial means restricted to the lab. This would spur research into the uses of CRISPR in the 50% of bacteria that do not possess their own CRISPR Cas systems. There is also a need for a method that could be used in situ, such as at the site of infection.

*Pseudomonas aeruginosa* and *Staphylococcus aureus* are important pathogens in cystic fibrosis (CF). Significant medical advances over the past several decades have improved key clinical metrics, quality of life, and longevity in patients with CF. More recently, the development and deployment of highly effective modulator (HEM) therapy aimed at ameliorating the underlying CF transmembrane conductance regulator (CFTR) protein defect have changed the clinical landscape in CF, improving patients' symptoms, lessening treatment burden, and enhancing quality of life. Yet, even so, there continues to be significant morbidity and mortality in CF. Pulmonary disease is the most significant contributor to morbidity in CF, and pulmonary infection is a significant driver of pulmonary disease in CF. (Zemanick, et al., *Cystic Fibrosis: Microbiology and Host Response*, 2016.) Respiratory care includes antibiotics, chest physiotherapy, medications to enhance secretion clearance, and anti-inflammatory medications. (Mogayzel, et al., *Cystic fibrosis pulmonary guidelines. Chronic medications for maintenance of lung health*, 2013; Flume, et al., *Cystic Fibrosis pulmonary guidelines: airway clearance therapies*, 2009.) While administration of antibiotics is undoubtedly part of the reason for improvement in longevity in CF over the past decades, (Davis, P. B., M. Drumm, and M. W. Konstan, Cystic fibrosis. Am J Respir Crit Care Med, 1996. 154(5): p. 1229-56; Simon, R. Cystic fibrosis: Antibiotic therapy for chronic pulmonary infection), pulmonary infection in CF continues to be a major problem and significantly contribute to morbidity and mortality in CF.

CF patients remain susceptible to colonization/infection with *Pseudomonas aeruginosa* (PsA). The prevalence of PsA infection increases with age and can happen as early as the first year of life, and approximately 60% of adults with CF become infected with PsA, although this trend may be decreasing in adolescent and adult patients in the United States. In the same vein, colonization/infection with *Staphylococcus aureus* (SA) is also common in CF. SA is the most frequent respiratory pathogen identified in children with CF. In addition, methicillin-resistant SA (MRSA) has increased significantly in prevalence, with 9.2% of patients with respiratory cultures positive in 2002 versus 24.6% in 2019.

New therapies targeting PsA and MSSA/MRSA in CF are needed. The deleterious impact of chronic infection with PsA and SA on lung function, pulmonary exacerbations, and hospitalizations raises the importance of developing effective treatment strategies for these pathogens. Currently, prevention of PsA acquisition and eradication therapy is key. (Mogayzel, P. J., Jr., et al., *Cystic Fibrosis Foundation pulmonary guideline. pharmacologic approaches to prevention and eradication of initial Pseudomonas aeruginosa infection*. Ann Am Thorac Soc, 2014.) However, despite optimal therapies, chronic PsA infection is common. In addition, eradication strategies for PsA are limited, and over time PsA can develop resistance mechanisms against most, if not all, available antibiotics. Moreover, long-term infection is characterized by virulence factors and formation of biofilms.

SUMMARY

In accordance with the purposes of the disclosed materials and methods, as embodied and broadly described herein, the disclosed subject matter, in one aspect, relates to methods of using a novel zinc porphyrin, ZnPor (II) as an anti-microbial.

Thus, in one example, the present disclosure provides a method of inhibiting the growth of a microorganism including contacting the microorganism with zinc porphyrin (ZnPor (II)).

In a further example, the present disclosure provides a method of treating or preventing biofilm formation of one or more microorganisms including contacting the biofilm with zinc porphyrin (ZnPor).

In a further example, the present disclosure provides a method of treating a disease associated with biofilm formation in a subject including administering to the subject a composition comprising a therapeutically effective amount of ZnPor.

The present disclosure relates to a small molecule that is highly effective at killing a wide range of bacteria (Gram-negative, Gram-positive, and Acid-fast bacteria). Additionally, this molecule, a Zn-containing porphyrin, can inactivate bacteriophage, and prevent a Coronavirus isolated from a common cold from infecting human cells in vitro. In 8 years of testing against model bacterium *Pseudomonas aeruginosa* (PsA), resistance has not developed. This is notable as PsA spp. have multiple resistance mechanisms (e.g., dozens of efflux pumps), and have developed resistance readily to those antibiotics it is exposed to for even short periods of time. ZnPor (II) enables activity of extant antibiotics that are ineffective against bacterial biofilms, e.g., Tobramycin. Further, the ZnPor (II) expands the range of bacteria killed by extant antibiotics such as Vancomycin. Vancomycin is not effective against Gram-negative bacteria; however, when pre-treated by ZnPor (II) this antibiotic kills the Gram-negative bacterium PsA. Additionally, ZnPor (II) can act synergistically with bacteriophage, via Phage Antibiotic Synergy (PAS), which has potential value in phage therapy. ZnPor (II) molecules also have a wide range of activities useful in research, based upon its ability to permeabilize bacteria when used at sub-lethal concentrations. This allows delivery of molecules into bacterial cells. These include DNA, bacteriophage and CRISPR components. Essentially, ZnPor (II) renders bacterial cells competent vis-à-vis the uptake of extracellular DNA (phage genomic DNA, plasmids, and even whole bacteriophage).

The present disclosure has the following valuable functions and characteristics: 1) potent antimicrobial activity that does not require light activation, or oxygen; 2) significant synergy with lytic bacteriophage making ZnPor a candidate for PAS applications against infections; 3) inactivation of bacteriophage and a Coronavirus; and 4) valuable research capabilities, e.g., to render bacteria competent to take up exogenous DNA including whole genomes of phage.

Further, ZnPor (II) can be used to broaden the host-range of a phage and can eliminate resistance when used together. Thus ZnPor (II)+PEV2 is an effective example Phage Antibiotic Synergy (PAS).

ZnPor (II) can also act directly to make bacterial cells more permeable at concentrations at or below the MIC. As ZnPor (II) is water soluble, it can be added to cells in vitro or in vivo to make cells "competent", able to take up (be transformed by) DNA and even whole phage. ZnPor (II) could be used in situ to deliver DNA, phage, even the CRISPR-Cas components on a plasmid.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying figures, which are incorporated in and constitute a part of this specification, illustrate several aspects described below.

(FIGS. 1D-1F). PsA biofilm contained within CF airways visualized by peptide nucleic acid FISH (PNA) and DAPI. (FIGS. 1D-1E) Biofilm and (FIG. 1F) intact bronchiolar wall are shown.

FIG. 2A: ZnPor (alone) stained biofilm. Biofilm was incubated in 8 µg/ml ZnPor solution for 2 h. The distribution of ZnPor in the biofilm was imaged by ZnPor excitation/emission (433 nm/620 nm respectively). The 3D volumetric depth image shows ZnPor is distributed throughout the biofilm matrix. FIG. 2B: LIVE/DEAD stain and 3D volumetric depths of biofilms treated with concentrations of ZnPor from 4 µg/ml to 64 µg/ml for 2 hours followed by LIVE/DEAD staining. FIG. 2C: LIVE/DEAD™ stain of biofilm treated with 100 µg/ml of Tobramycin alone, or in combination with ZnPor [30 minutes pre-treatment (4 µg/ml)] for 2 hours. Biofilm treated with ZnPor alone (4 µg/ml) is shown in panel B. Control refers to a biofilm that received no treatment. All graphs are representative of three independent experiments (n=9). Length of size bar: 10 µM.

FIG. 3A(I) represents PsA Biofilm: a16-18-hour biofilm imaged after treatment with the LIVE/DEAD stain: a thick layer of cells encased in a matrix (ECM). All or almost all cells are green from the LIVE/DEAD stain. The ECM contains a variety of different biomolecules e.g., eDNA, which constitutes the majority of the ECM. ZnPor can diffuse throughout the ECM (as shown in FIG. 3A(II)) and thus interact with the eDNA in the matrix. FIGS. 3A(II) and (III) ZnPor treatment (prior to LIVE/DEAD) has the effect of destabilizing the biofilm, and ultimately the biofilm sloughs off the surface (II & III). LIVE/DEAD stained biofilms depict dead biofilm-associated cells left on the surface after ZnPor treatment. Overall, the matrix of biofilms treated with ZnPor are converted from a thick and dense matrix to a thin monolayer of almost exclusively dead cells and detachment of the biofilm from the surface. FIG. 3B: Individual planktonic PsA cells rapidly accumulate ZnPor in the cytoplasm and membrane/cell wall. Porphyrins bind to DNA either intercalating and/or binding to the outside of the helix. ZnPor treated cells do not increase in total number (nor do they decrease); these cells do not form colonies when plated onto LB agar plates thus are not viable. Yet the cells do not lyse. The intact dead cells can be handled by the immune system and better than lysing the cells due to the release of endotoxin.

FIG. 8 shows the assays that can be used for cell death pathway analysis. BAX, BCL-2-like protein 4; BCL-2, B cell lymphoma-2; BCL-XL, B cell lymphoma-extra large; Bid, BH3 interacting-domain death agonist; Bim, BCL-2-like protein 11; LDH, lactate dehydrogenase; MCL-1, myeloid-cell leukemia 1; PARP, poly (ADP-ribosyl) polymerase; PI, propidium iodide; TRAIL, tumor necrosis factor (TNF)-related apoptosis-inducing ligand; TNF, tumor necrosis factor; TNFR1, TNF receptor 1; TRAILR1, TRAIL receptor 1; TUNEL, terminal dUTP nick end labeling.

FIG. 9 shows measurements of acute lung injury that can be used to assess efficacy of ZnPor in PsA and SA infection. HE, hematoxylin-eosin; LDH, lactate dehydrogenase.

Figures 15A, 15B:
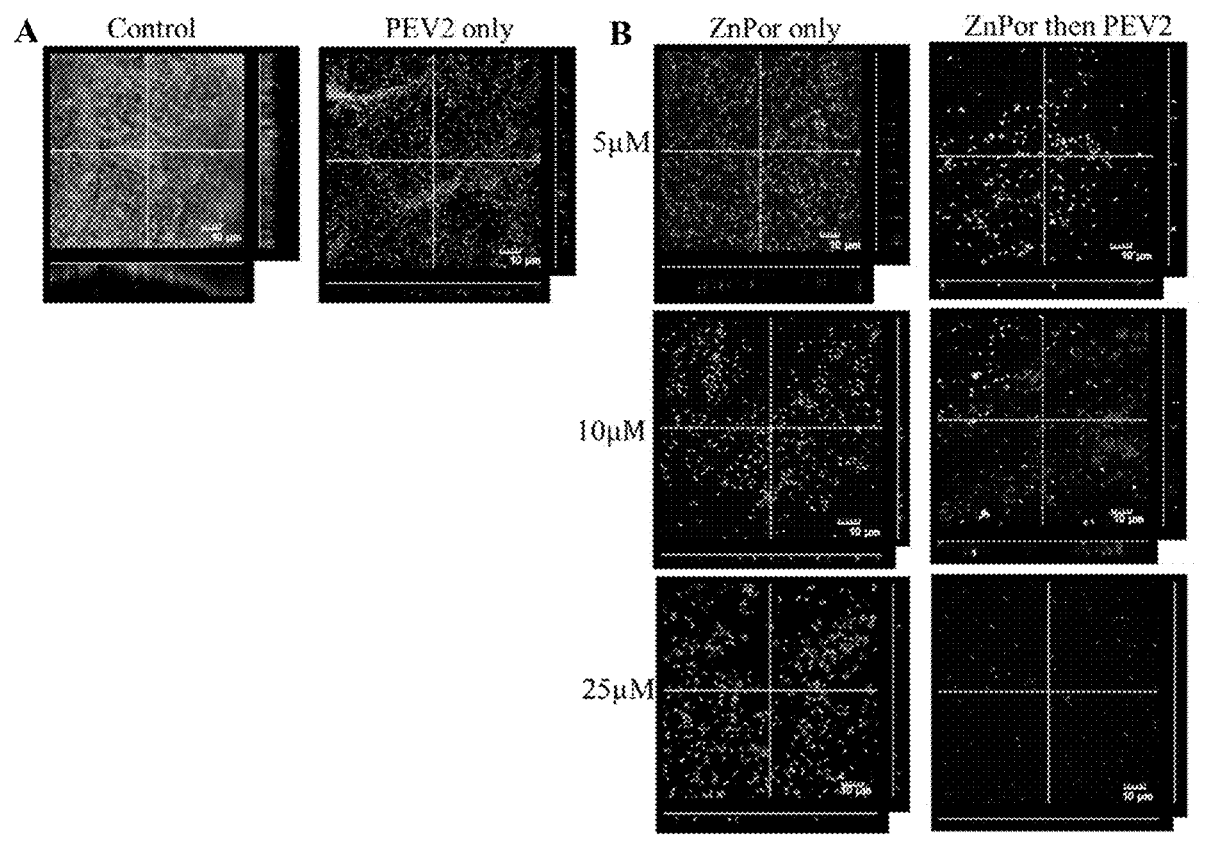

FIGS. 15A-15B show the biofilms of PAO1 treated with various concentrations of ZnPor (II) and in combination with PEV2 phage. Biofilms of strain PAO1 were grown on coupons cut from polyethylene in MSG media for approximately 16-18 hours. Overnight media was replaced with fresh PBS and were treated with (FIG. 15B) ZnPor (II) only at concentrations of 5, 10 or 25 μg/mL, and incubated for 2 h, (FIG. 15A) phage PEV2 only (MOI=10:1) for 4 h, or (FIG. 15B) ZnPor (II) treatment for 2 h followed by the addition of phage PEV2 (MOI of 10:1) and incubated for an additional 4 h. Coupons were gently washed in distilled water and were treated with LIVE/DEAD™ stain. All coupons were imaged using confocal laser scanning electron microscopy (CLSM) at 60×. Green=LIVE Red=DEAD. Control refers to a biofilm that received no treatment.

FIGS. 17A-17B show viable cell counts (CFU per ml) (FIG. 17A) and phage (PFU per ml) (FIG. 17B) of Biofilm cells treated with ZnPor (II) and/or phage PEV2, with and without photoactivation.

FIG. 18A is a control, FIG. 18B was treated with PEV2 phage only, at MOI 10:1, FIG. 18C was treated with tobramycin at 25 μg/mL, FIG. 18D was treated with ZnPor (II) at 25 μg/mL, FIG. 18E was treated with tobramycin and PEV2, and FIG. 18F was treated with ZnPor (II) and PEV2.

(FIG. 19A) Control (no additions), (FIG. 19B) ZnPor (25 μg/mL) for 2 hours, (FIG. 19C) Phage PEV2 (MOI of 10:1) for 4 hours, or (FIG. 19D) ZnPor (25 μg/mL) for 2 hours followed by the addition of Phage PEV2 (MOI of 10:1) for 4 hours. Coupons were gently washed in distilled water and were treated with LIVE/DEAD™ stain. All coupons were imaged using confocal laser scanning electron microscopy (CLSM) at 60×. These figures show that ZnPor (II) treatment can make PA14 cells sensitive to PEV2 phage.

FIGS. 20A-20B shows biofilms of PsA PAO1 treated with ZnPor (II) at 4 μg/mL MIC (FIG. 20A); or ZnPor (II) at 4 μg/mL followed by the addition of whole phage PEV2 or purified genomic DNA of PEV2 (FIG. 20B). PAO1 was grown overnight in MSG at 37 C with shaking. CDC Bioreactors with PE coupons were inoculated to a final OD of 0.15 in cation adjusted Mueller Hinton broth. Biofilms were grown 16-18 h at 37 degrees C. with 50 rpm stirring. Control biofilm is shown (FIG. 20A). All overnight media in bioreactors were replaced with fresh PBS. Bioreactors treated with ZnPor (II) at 4 μg/mL were left to incubate for 2 hours without stirring. Bioreactors treated with either whole PEV2 phage or the purified DNA genome of PEV2 were incubated for 24 hours without stirring. This differs from FIGS. 15A-15B in that the incubation time was 4 hours in FIGS. 15A-15B. This change was made because the DNA genome was expected to take longer to make whole virions. Bioreactors containing ZnPor (II) at 4 μg/mL (FIG. 20B) were incubated for 2 hours upon which the spent medium was replaced with fresh PBS to remove ZnPor (II). Purified genomic DNA from PEV2 phage was added to reactors or whole phage of PEV2 and incubated without stirring for 24 h. Coupons were removed, gently rinsed with ddH2O before staining with LIVE/DEAD stain and viewed using a CLSM.

Biofilms treated with only the PEV2 whole phage (FIG. 20A) have many live PAO1 cells (GREEN) and there appears to be a great deal of "debris" left on the surface of the substrata. In contrast, in FIG. 20B where biofilms were pre-treated with ZnPor (II) before adding the PEV2, whole phage are only dead cells, as all are red, and it appears to be a monolayer. PEV2 is an obligately lytic phage and so infected cells lyse/burst releasing cell contents including cell wall/envelope materials such as LPS which is a potent endotoxin. Further the debris can promote recolonization of the biofilm on such substrata. Biofilms pre-treated with ZnPor (II) at the MIC (4 μg/mL) are a monolayer of dead cells.

These experiments were done using ZnPor (II) at 4 μg/ml which is the MIC; PAO1 cells are made permeable at this concentration but few are killed, e.g., it is acting as a static agent. In the other experiments shown above ZnPor (II) was used at 25 μg/ml which is a bactericidal concentration. The difference between using 25 and 4 μg/mL ZnPor. At 25 μg/mL ZnPor alone there is almost complete clearing of the biofilm leaving a monolayer of dead un-lysed cells in 2 h. At 4 μg/mL for 24 h there is more than a monolayer of cells, many not dead. Yet the combination of ZnPor+PEV2 phage exhibits substantial synergy. The genomic DNA-only biofilms have rosettes of red (DEAD) cells, which can be likened to how plaques form in populations of the host cells in soft agar. Pretreatment with ZnPor+genomic DNA results in far more killing and infective phage are produced. We collected samples from the biofilms and used phage isolation and purification techniques followed by plaque assay soft-agar technique. Plaques were detected in the ZnPor+genomic DNA of PEV2.

Figure 21:

FIG. 21 shows phage plaques produced from transformation of PEV2 genomic DNA into biofilm cells of PAO1 after treatment of biofilms with ZnPor (II). Samples were plated using agar overlays. The small clear zones are plaques. This shows that genomic DNA from phage PEV2 did get into cells pre-treated with ZnPor (II) at MIC levels. And productive phage are produced in the PAO1 cells. This is proof of principle that ZnPor renders cells able to take up exogenous DNA. And that the whole genome was taken up by cells is evidence that this method allows for by-passing the phage specific receptors on the cell surface. This opens up the possibility of using ZnPor treatment to by-pass the specificity of phage-cell receptor needed for infection. Thus, making phage able to infect a wider range of bacterial cells. Even cocktails of phage genomes could be used to further broaden the range of bacteria phage can infect and destroy in infections.

Figures 22A, 22B:
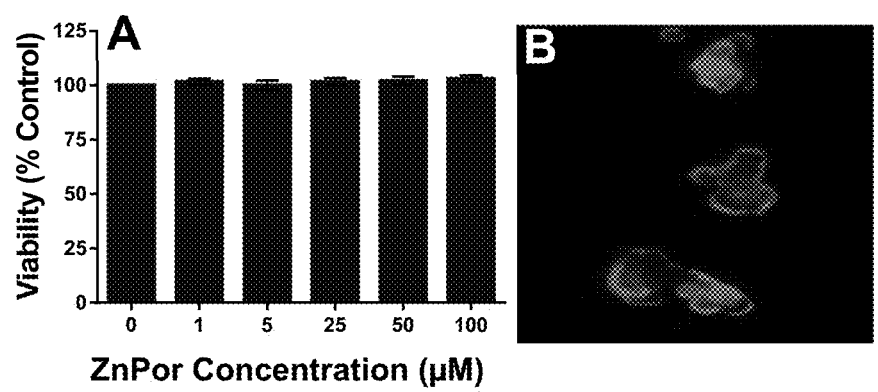

FIGS. 22A-22B show a lung co-culture (A549/U937) model after 24 hour exposure to ZnPor displaying no toxicity (FIG. 22A) and U937 stained and imaged after 24 hours of dark exposure to 50 μM ZnPor (FIG. 22B). The pink indicates intracellular localization, demonstrating active endocytosis. Taken together these results demonstrated the ZnPor was internalized by macrophages, but not eliciting a harmful response.

Figures 23A, 23B, 23C:
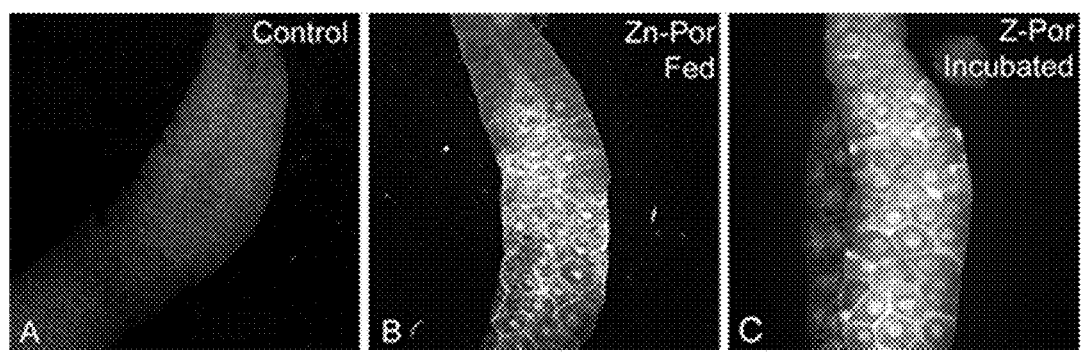

FIGS. 23A-23C show ZnPor localized to the nucleus membrane. More specifically, they show salivary glands from third instar larvae of Drosophila melanogaster. FIG. 23A is the control (no ZnPor), FIG. 23B fed 5 mM ZnPor and dissected after 24 h, and FIG. 23C shows salivary glands dissected from third instar larvae that were directly incubated in ZnPor for 4 h and confirms the localization of ZnPor to both the cell membrane and nuclei. Treatment with ZnPor did not result in any observed toxicity.

Figure 24:
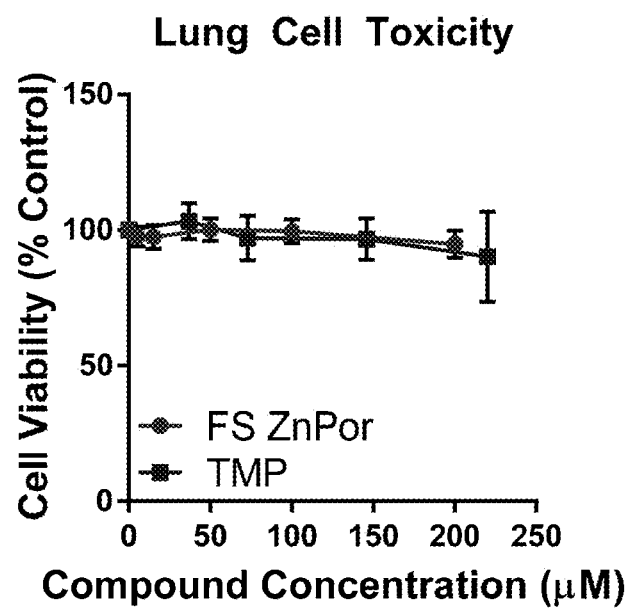

FIG. 24 shows a lung cell toxicity graph. Sample represented in graph is a traditional cell culture model and the cells were A549 cells—human lung epithelial cells. No toxicity was observed at concentration exceeding therapeutic range.

Figure 25:
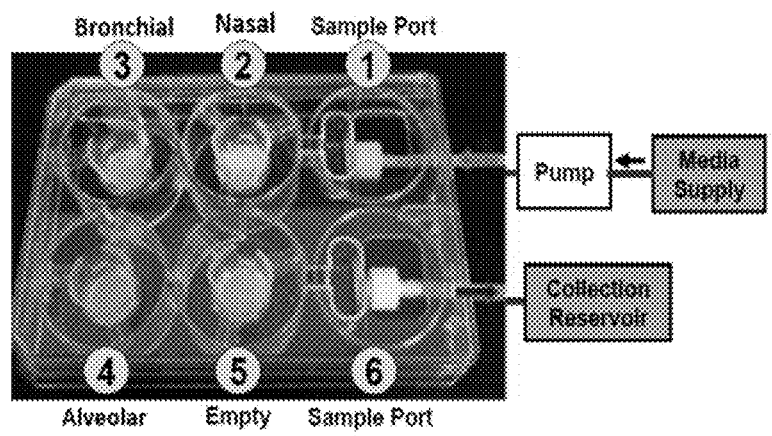

FIG. 25 shows an inhalation based perfusion platform that includes interconnected nasal, bronchial, and alveolar 3-D cellular compartments, which is evolved from testing that includes evaluating ZnPor safety within a lung co-culture model (epithelial/macrophage).

FIGS. 26A-26B shows a microdilution model for antimicrobial susceptibility testing for bacteria: S. aureus (MRSA) (FIG. 26A) and S. aureus (MRSA) (FIG. 26B) that grow aerobically.

Figure 27:
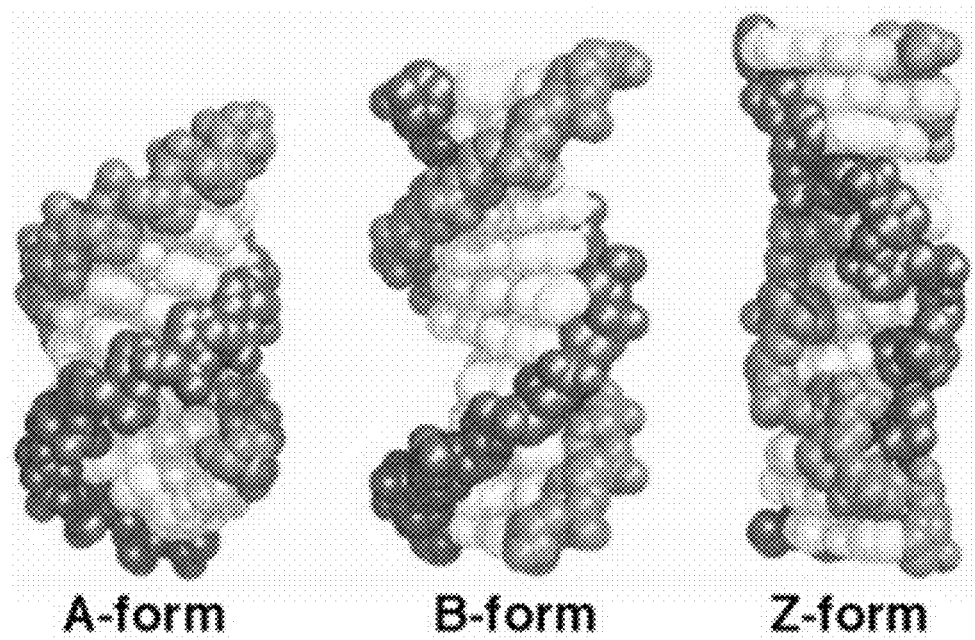

FIG. 27 shows three major forms of DNA: A-form, B-form, and Z-form.

Figure 28:
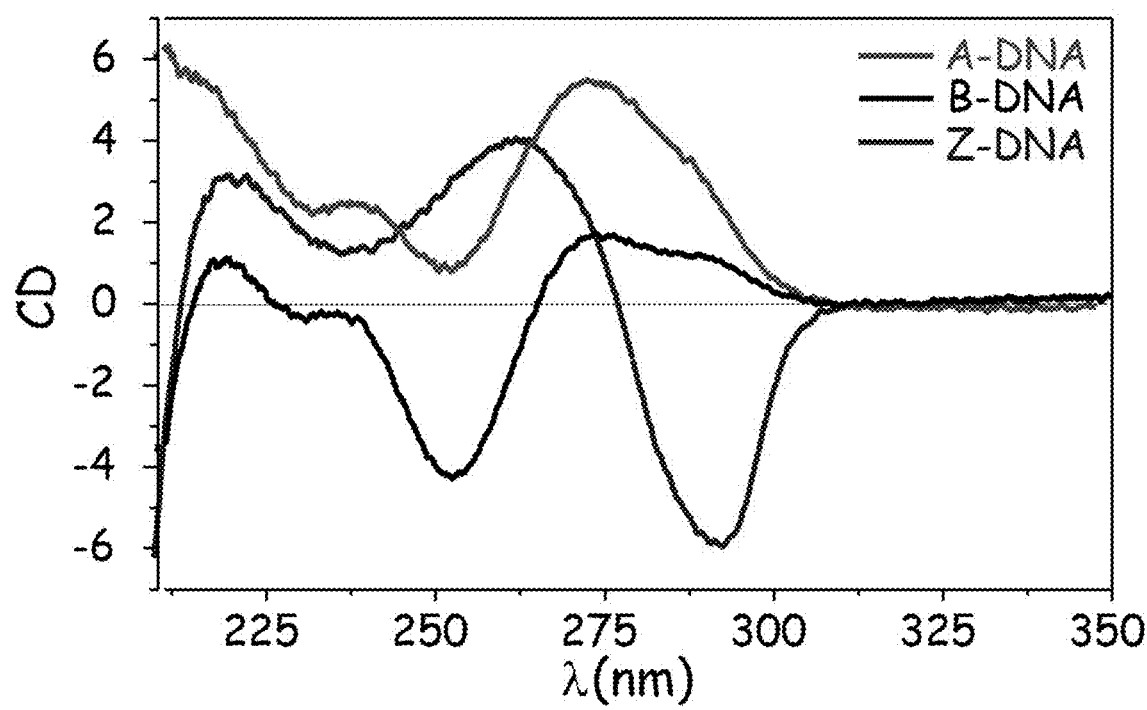

FIG. 28 shows circular dichroism (CD) spectra of DNA.

Figures 29A, 29B, 29C:
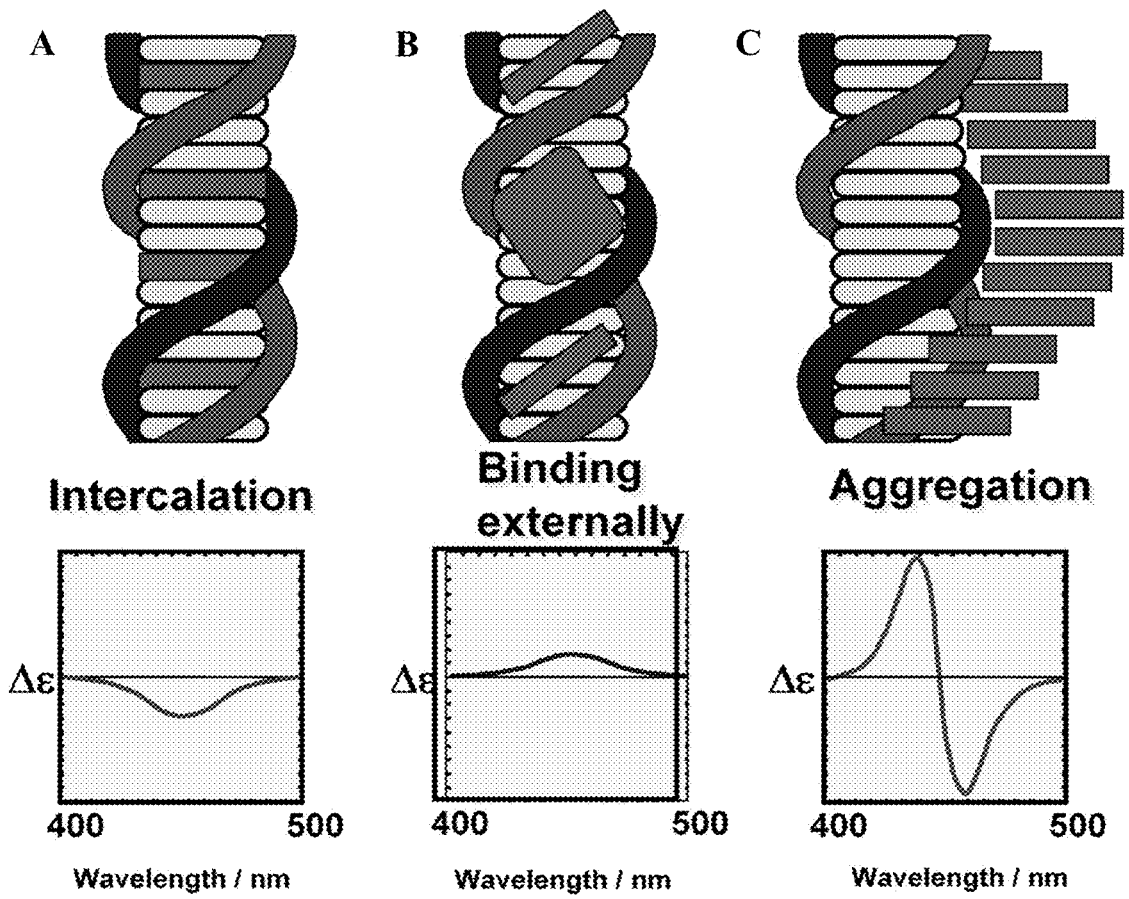

FIGS. 29A-29C shows CD spectra of porphyrin binding with DNA: FIG. 29A is intercalation, FIG. 29B is binding externally, and FIG. 29C is aggregation.

Figures 30A, 30B:
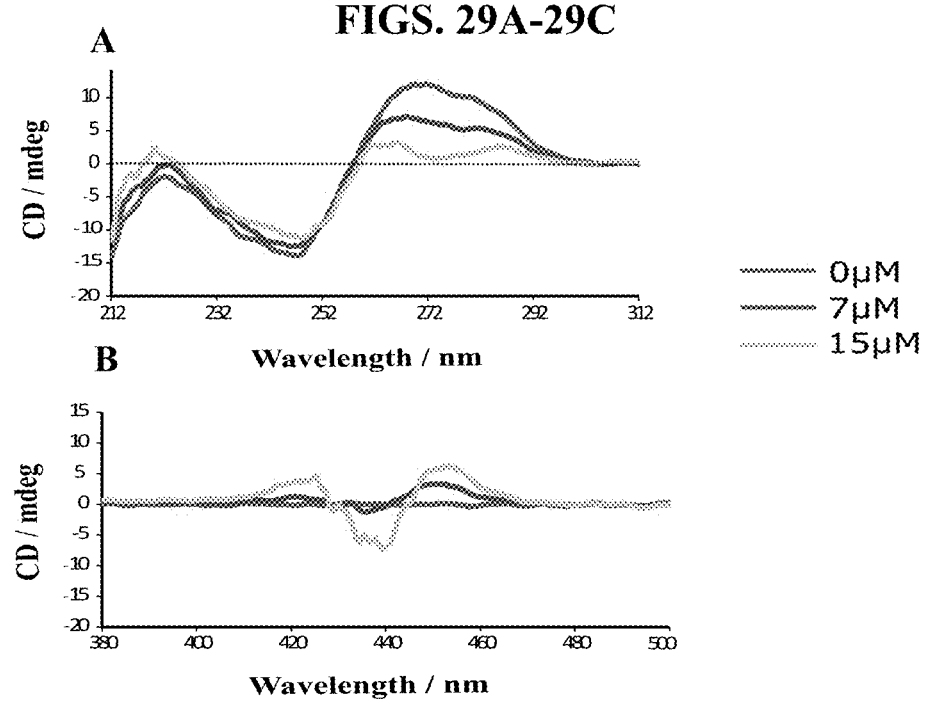

FIGS. 30A-30B shows binding interaction of ZnPor with PsA DNA: FIG. 30A shows wavelengths from 212 nm-312 nm and FIG. 30B shows wavelengths from 380 nm to 500 nm.

Figures 31A, 31B, 31C, 31D:
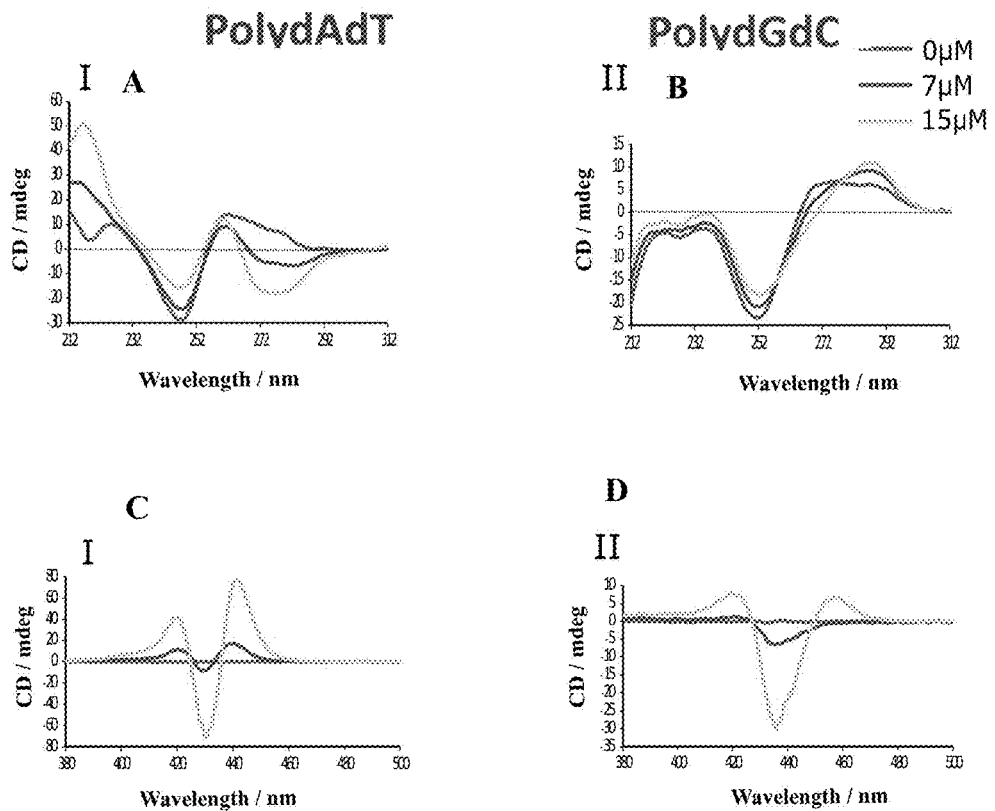

FIGS. 31A-31D shows sequence preference of ZnPor: FIG. 31A shows CD with PolydAdT from 212 nm to 312 nm; FIG. 31B shows PolydGdC from 212 nm to 312 nm; FIG. 31C PolydAdT shows from 380 nm to 500 nm; and FIG. 31D shows PolydGdC from 380 nm to 500 nm.

Figures 32A, 32B, 32C, 32D:
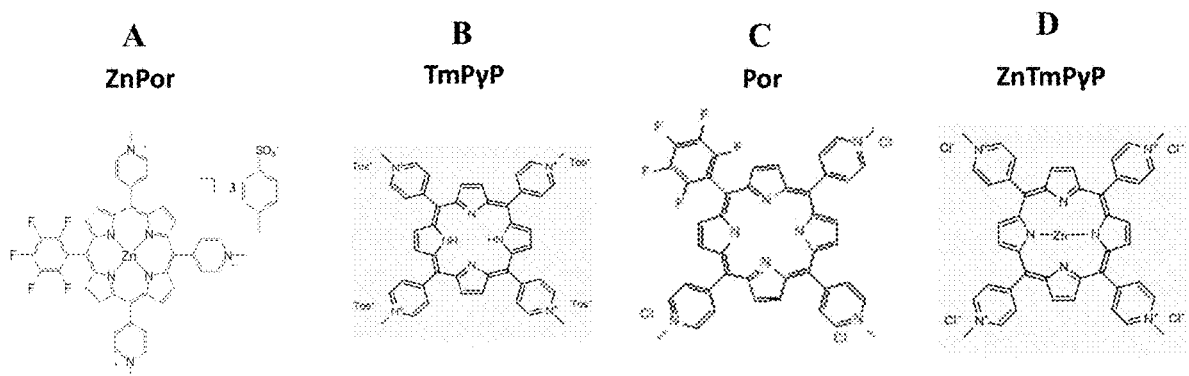

FIGS. 32A-32D shows ZnPor analogs: FIG. 32A is ZnPor, FIG. 32B is TmPyP, FIG. 32C is Por, and FIG. 32D is ZnTmPyP.

Figures 33A, 33B, 33C, 33D:
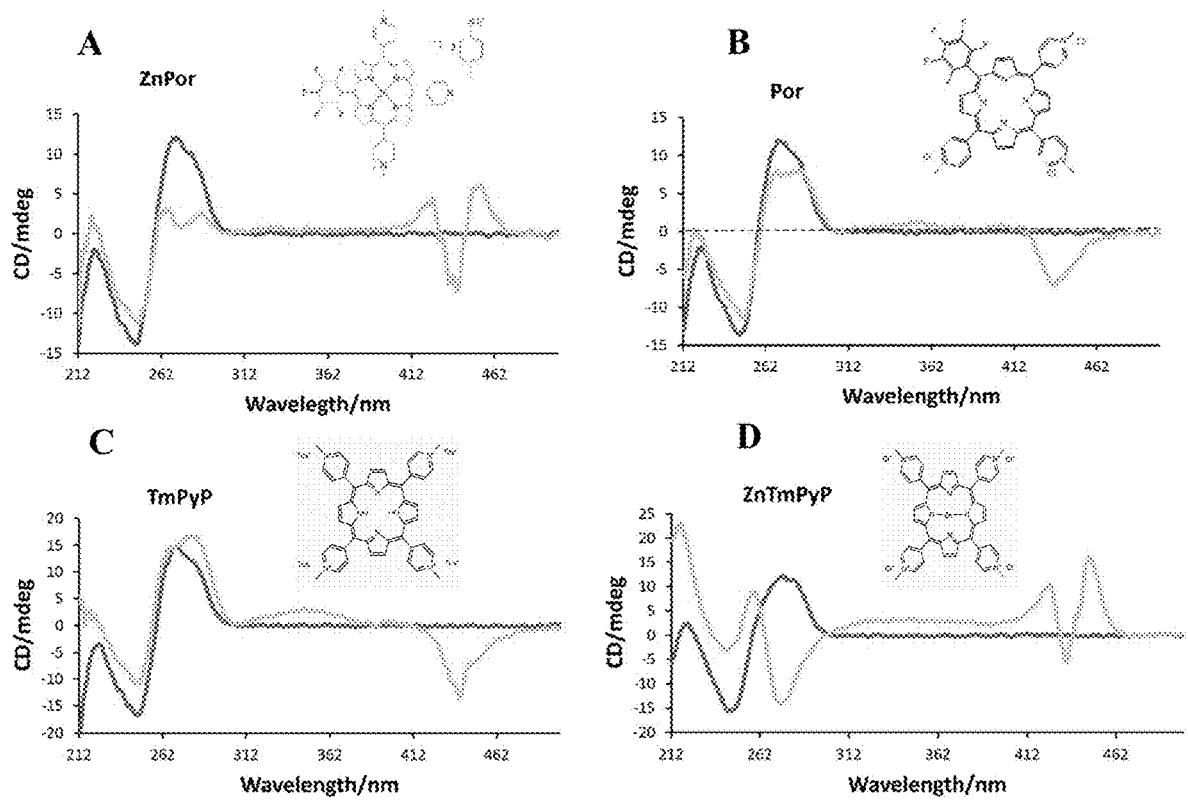

FIGS. 33A-33D shows the role of zinc and flouridyl groups in binding with PsA DNA: FIG. 33A shows ZnPor, FIG. 33B shows Por, FIG. 33C shows TmPyP, and FIG. 33D shows ZnTmPyP.

Figure 34:
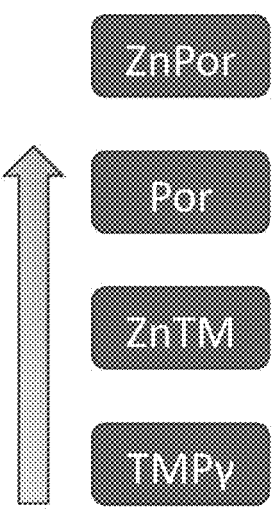

FIG. 34 shows the relative levels of efficacy of ZnPor, Por, ZnTm, and TmPy. Efficacy was determined by standard kill assays.

DETAILED DESCRIPTION

The following description of the disclosure is provided as an enabling teaching of the disclosure in its best, currently known embodiments. Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As can be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It can be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

An "increase" can refer to any change that results in a greater amount of a symptom, disease, composition, condition, or activity. An increase can be any individual, median, or average increase in a condition, symptom, activity, composition in a statistically significant amount. Thus, the increase can be a 1, 2, 3, 4, 5, 6, 7, 8, 9, 10, 15, 20, 25, 30, 35, 40, 45, 50, 55, 60, 65, 70, 75, 80, 85, 90, 95, or 100% increase so long as the increase is statistically significant.

A "decrease" can refer to any change that results in a smaller amount of a symptom, disease, composition, condition, or activity. A substance is also understood to decrease the genetic output of a gene when the genetic output of the gene product with the substance is less relative to the output of the gene product without the substance. Also, for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

The term "subject" refers to any individual who is the target of administration or treatment. The subject can be a vertebrate, for example, a mammal. In one aspect, the subject can be human, non-human primate, bovine, equine, porcine, canine, or feline. The subject can also be a guinea pig, rat, hamster, rabbit, mouse, or mole. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "treat" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

"Biocompatible" generally refers to a material and any metabolites or degradation products thereof that are generally non-toxic to the recipient and do not cause significant adverse effects to the subject.

"Comprising" is intended to mean that the compositions, methods, etc. include the recited elements, but do not exclude others. "Consisting essentially of" when used to define compositions and methods, shall mean including the recited elements, but excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions provided and/or claimed in this disclosure. Embodiments defined by each of these transition terms are within the scope of this disclosure.

A "control" is an alternative subject or sample used in an experiment for comparison purposes. A control can be "positive" or "negative."

"Effective amount" of an agent refers to a sufficient amount of an agent to provide a desired effect. The amount of agent that is "effective" will vary from subject to subject, depending on many factors such as the age and general condition of the subject, the particular agent or agents, and the like. Thus, it is not always possible to specify a quantified "effective amount." However, an appropriate "effective amount" in any subject case may be determined by one of ordinary skill in the art using routine experimentation. Also, as used herein, and unless specifically stated otherwise, an "effective amount" of an agent can also refer to an amount covering both therapeutically effective amounts and prophylactically effective amounts. An "effective amount" of an agent necessary to achieve a therapeutic effect may vary according to factors such as the age, sex, and weight of the subject. Dosage regimens can be adjusted to provide the optimum therapeutic response. For example, several divided doses may be administered daily, or the dose may be proportionally reduced as indicated by the exigencies of the therapeutic situation.

A "pharmaceutically acceptable" component can refer to a component that is not biologically or otherwise undesirable, e.g., the component may be incorporated into a pharmaceutical formulation provided by the disclosure and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

"Pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

"Therapeutic agent" refers to any composition that has a beneficial biological effect. Beneficial biological effects include both therapeutic effects, e.g., treatment of a disorder or other undesirable physiological condition, and prophylactic effects, e.g., prevention of a disorder or other undesirable physiological condition (e.g., a non-immunogenic cancer). The terms also encompass pharmaceutically acceptable, pharmacologically active derivatives of beneficial agents specifically mentioned herein, including, but not limited to, salts, esters, amides, proagents, active metabolites, isomers, fragments, analogs, and the like. When the terms "therapeutic agent" is used, then, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

"Therapeutically effective amount" or "therapeutically effective dose" of a composition (e.g., a composition comprising an agent) refers to an amount that is effective to achieve a desired therapeutic result. In some embodiments, a desired therapeutic result is the control of type I diabetes. In some embodiments, a desired therapeutic result is the control of obesity. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as pain relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

It should be noted that ratios, concentrations, amounts, and other numerical data can be expressed herein in a range format. It can be further understood that the endpoints of each of the ranges are significant both in relation to the other endpoint, and independently of the other endpoint. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "0.1% to 5%" should be interpreted to include not only the explicitly recited values of 0.1% to 5%, but also include individual values (e.g., 1%, 2%, 3%, and 4%) and the sub-ranges (e.g., 0.5% to 1.1%; 5% to 2.4%; 0.5% to 3.2%, and 0.5% to 4.4%, and other possible sub-ranges) within the indicated range.

Methods
Method of Inhibiting Growth of a Microorganism

Provided herein is a method of inhibiting the growth of a microorganism including contacting the microorganism with zinc porphyrin (ZnPor).

As used herein, "microorganisms" include, but are not limited to, bacteria, viruses, fungi, algae, yeasts, protozoa, spirochetes, single-celled and multi-celled organisms that are included in classification schema as prokaryotes, eucaryotes, Archaea, Bacteria and those that are known to those skilled in the art. Microorganisms may also refer to isolated microorganisms and may comprise particular deposited compositions or microorganisms disclosed herein, and the intent of the text can be interpreted by those of skill in the art.

As used herein, "porphyrins" are tetrapyrroles macrocycles capable of binding metal ions. Porphyrins can exhibit diverse functions in nature as, for example, 1) the heme in hemoglobin, a porphyrin with an Fe ion in the center or 2) the active center of chlorophyll, a Mg-containing porphyrin. The chlorophyll porphyrin can enable the organism to harvest light for the production of energy compounds. In both cases, while different from each other, the porphyrin, or catalytic center, can serve as the "business part" of both heme and chlorophyll molecules. Porphyrins can also be found in cytochromes in bacteria and animals, such as the P450 class of enzymes. In the case of cytochromes, the porphyrin can mediate necessary redox functions in cells that result in the organism producing energy via an electron transport chain.

Porphyrins have the General Formula

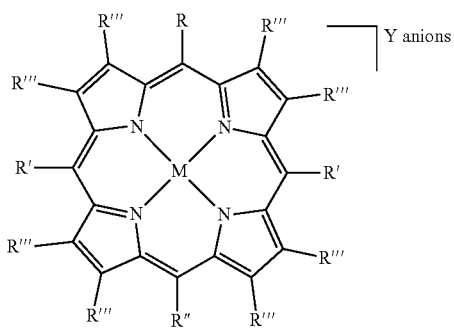

wherein,
M is a transition metal (II) cation,
R is a mono-, di-, tri-, tetra-, or pentahalophenyl and the halogen is selected from the group comprising Cl, F, Br, and combinations thereof,
R' is

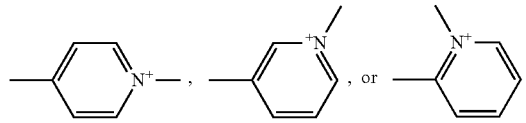

R" is equal to R or R',
R'" is —H, —F, —Cl, or —Br, and
Y is 2 or 3.

As used herein, "ZnPor", also "ZnPor (II)" or "zinc porphyrin", refers to an embodiment of the porphyrins disclosed herein that includes a $Zn^{+2}$ transition metal cation. ZnPor of the present disclosure is described in, for example, U.S. Pat. No. 9,364,537, which is incorporated herein by reference. In one embodiment, M is selected from the group consisting of $Fe^{+2}$, $CO^{2+}$, $Ni^{+2}$, and $Zn^{+2}$. In another embodiment, R" is equal to R' and M is $Zn^{+2}$, and further R' is N-methyl-4-pyridyl, R is pentfluorophenyl, and R'" is —H. The porphyrin can also include anions to neutralize the charges on the ring. In one embodiment, Y is 3 and the anions are each p-toluene sulfonate. This porphyrin is a meso-5,10,15-tris(N-methyl-4-pyridyl)-20-(pentafluorophenyl)porphyrinatozinc(II), tris-p-toluene sulfonate (ZnPFPTMP) and shown

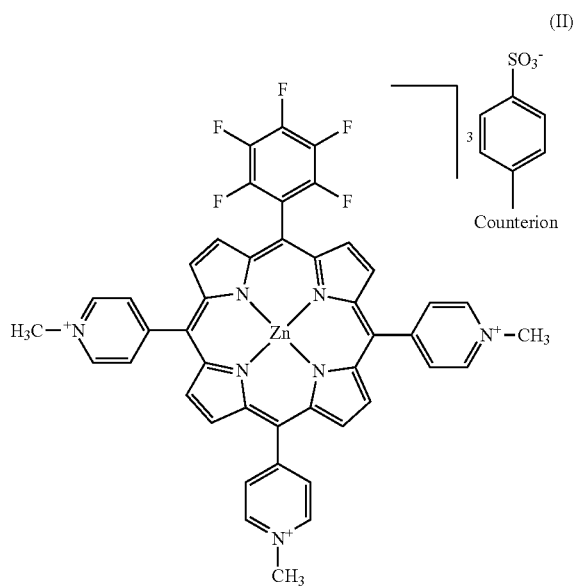

below.

In a further embodiment, M is $Zn^{+2}$, R" is equal to R and R is pentfluorophenyl, and further R' is N-methyl-4-pyridyl, R'" is —H, Y is 2 and the anions are each p-toluene sulfonate. This porphyrin is a meso-5, 15-di(N-methyl-4-pyridyl)-10,20-di(pentafluorophenyl)porphyrinatozinc(II), di-p-toluene sulfonate and shown below.

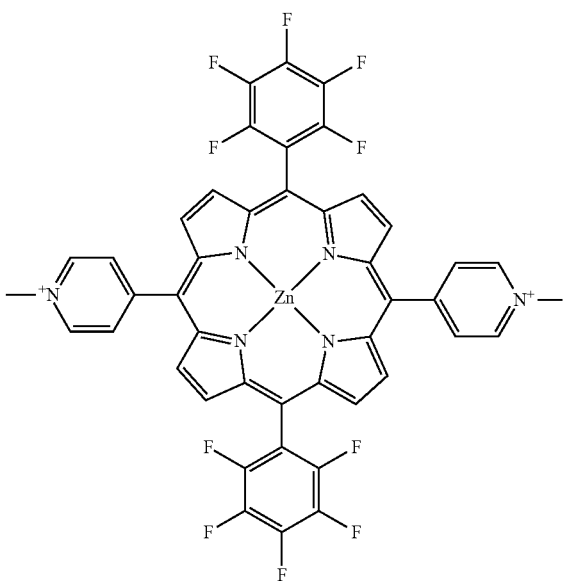

In some embodiments, the method can further include enhancing the efficacy of the ZnPor using light activation from 380 nm to 700 nm. In certain embodiments, ZnPor can undergo light activation from 420 nm to 430 nm. In further embodiments, inhibition of the microorganism with ZnPor does not require light activation. In some embodiments, ZnPor (II) can undergo light activation with visible light having from 200 W to 400 W.

As used herein, "light activation" is used to refer to the process of using light to activate porphyrins, including methods such as antimicrobial photodynamic therapy (aPDT). In aPDT, visible light activates the porphyrin, resulting in generation of reactive oxygen species (ROS) that kill bacteria via an oxidative burst. The visible light can be provided with low power lasers. In further embodiments, the visible light can have from 200 W to 400 W, 250 W to 350 W, 275 W to 325 W, or 290 W to 310 W. In some embodiments, cationic porphyrins can kill bacterial cells when photoactivated via production of ROS. Gram-positive (MSSA/MRSA), gram-negative (PsA, *Escherichia coli*), and fungi (e.g., *Candida albicans*) can be susceptible to light activated porphyrins. In certain embodiments, light activation, and more specifically aPDT, can be used against planktonic cells and/or biofilms.

In some embodiments, treating the microorganism with ZnPor does not require oxygen.

In certain embodiments, the ZnPor can be water soluble.

As used herein, "water soluble" refers to a property wherein a material is miscible in water, or in other words, is capable of forming a homogenous solution with water at ambient conditions.

In further embodiments, the microorganism can have no bacterial resistance to ZnPor.

As used herein, "bacterial resistance" is the ability of a microorganism like bacteria or fungi to withstand the effects of the antibiotics, biocides, or drugs that are intended to kill or control them. Three fundamental mechanisms of bacterial resistance include enzymatic degradation of antibacterial drugs, alteration of bacterial proteins that are antimicrobial targets, and changes in membrane permeability to antibiotics.

In some embodiments, the ZnPor can be not toxic to a human lung cell. In certain embodiments, the ZnPor can be not toxic to a human skin cell.

As used herein, "toxic" refers to the capacity of a substance or composition to be harmful, adverse, and/or poisonous to a cell, tissue, organ tissue, vasculature, or cellular environment, for example.

As used herein, "human cell" refers to the smallest unit that can live on its own, which makes up all the living organisms and tissues of the body. A human cell has three main parts: cell membrane, nucleus, and cytoplasm. As used herein, "human lung cell" refers to a cell from a human lung. Human lung cells can include bronchial and bronchiolar epithelium cells, alveolar unit cells, and pulmonary vascular cells. As used herein, "human skin cell" refers to a cell from human skin. Human skin cells can include keratinocytes, melanocytes, Langerhans cells, and Merkel cells.

In further embodiments, the ZnPor can be an anti-viral.

As used herein, "anti-viral" refers to drugs used for targeting viral infections. In some embodiments, anti-virals can target specific viruses. In other embodiments, anti-virals can be "broad spectrum", or in other words, effective against a wide range of viruses. In certain embodiments, anti-virals do not destroy the target virus, but instead inhibit its development.

In some embodiments, the microorganism being inhibited can be present on an inanimate surface. In certain embodiments, the inanimate surface can include solid surfaces, biomedical devices, titanium joints, dental instruments, catheters, and/or Endotracheal tubes. As used herein, "inanimate surface" refers to a surface that does not have the qualities of an active, living organism. In some embodiments, inanimate surface includes plastic, glass, fiber, or any combination thereof.

In further embodiments, the microorganism being inhibited can have infected a subject.

In some embodiments, the microorganisms can include bacteria, fungi, viruses, bacteriophage, or any combination thereof.

As used herein, "bacteria" refers to small single-celled microorganisms. Bacteria can be spheres, rods, or spirals. In some embodiments, bacteria are pathogenic, in which case they can cause diseases. Pathogenic bacteria can cause infectious diseases including, but not limited to, cholera, syphilis, anthrax, leprosy, tuberculosis, and tetanus. In other embodiments, bacteria are beneficial, such as those in the gut.

As used herein, "fungi" is used in reference to eukaryotic organisms such as the molds and yeasts, including dimorphic fungi, fungi found in soil, and any fungi found growing on a plant.

As used herein, "virus" refers to any large population of infectious entities that cannot grow or replicate without host cells. Viruses can contain a protein coat that surrounds the RNA or DNA core of genetic material, but do not contain a semi-permeable membrane and can only grow and replicate in living cells. Viruses include, but are not limited to, poxvirus, herpes virus, adenovirus, adeno-associated virus, lentivirus, retrovirus, rhabdovirus, papilloma virus, vesicular stomatitis virus, measles virus, Newcastle disease virus, picovirus Luna virus, Sindbis virus, papilloma virus, parvovirus, reovirus, coxsackie virus, influenza virus, mumps virus, poliovirus, Coronavirus, and Semliki Forest fever virus.

As used herein, "bacteriophage" refers to a virus that infects and replicates within bacteria and archaea. Bacteriophages are composed of proteins that encapsulate DNA or RNA genome and replicate within the bacterium following the injection of their genome into its cytoplasm. They can be used as an alternative to antibiotics and can be used as a possible therapy against multi-drug resistant strains of many bacteria via phage therapy. In some embodiments, bacteriophage can infect and kill bacteria in human or animal cells without having a negative effect on those cells.

In certain embodiments, the bacteria can include gram-negative bacteria, gram-positive bacteria, acid-fast bacteria, or any combination thereof.

As used herein, "gram-negative bacteria" refers to bacteria that turn red when Gram stain is applied to them. Gram-negative bacteria have a thin peptidoglycan layer as compared to gram-positive bacteria. Gram-negative bacteria include, but are not limited to, *Escherichia coli*, *Pseudomonas aeruginosa*, *Chlamydia trachomatis*, and *Yersinia pestis*.

As used herein, "gram-positive bacteria" refers to bacteria that turn blue when Gram stain is applied to them. Gram-positive bacteria have a thick peptidoglycan layer in comparison to gram-negative bacteria. Gram-positive bacteria include, but are not limited to, *Staphylococcus aureus*, *Streptococcus pyogenes*, and *Streptococcus* penumoniae.

As used herein, "acid-fast bacteria" refers to a group of bacteria that share the characteristic of acid fastness, wherein acid fastness is a physical property that gives a bacterium the ability to resist decolorization by acids during staining procedures. Therefore, acid-fast bacteria cannot be decolorized using acids routinely used in this process, which can allow for relatively easy classification and detection in laboratory procedures such as microscopy. Acid-fast bacteria include *Mycobacterium leprae*, *Mycobacterium smegmatis*, *Nocardia nova*, *Nocardia brasiliensis*, and *Nocardia farcinica*.

In further embodiments, the bacteria can include *Mycobacterium tuberculosis*, *Mycobacterium bovis*, *Mycobacterium bovis* strain BCG, BCG substrains, *Mycobacterium avium*, *Mycobacterium intracellular*, *Mycobacterium africanum*, *Mycobacterium kansasii*, *Mycobacterium marinum*, *Mycobacterium ulcerans*, *Mycobacterium smegmatis*, *Mycobacterium avium* subspecies paratuberculosis, *Nocardia asteroides*, other *Nocardia* species, *Legionella pneumophila*, other *Legionella* species, *Acetinobacter baumanii*, *Salmonella typhi*, *Salmonella enterica*, other *Salmonella* species, *Shigella boydii*, *Shigella dysenteriae*, *Shigella sonnei*, *Shigella flexneri*, other *Shigella* species, *Yersinia pestis*, *Pasteurella haemolytica*, *Pasteurella multocida*, other *Pasteurella* species, *Actinobacillus* pleuropneumonias, *Listeria monocytogenes*, *Listeria ivanovii*, *Bacillus subtilis*, *Brucella abortus*, other *Brucella* species, *Cowdria ruminantium*, *Borrelia burgdorferi*, *Bordetella avium*, *Bordetella pertussis*, *Bordetella bronchiseptica*, *Bordetella trematum*, *Bordetella hinzii*, *Bordetella pteri*, *Bordetella parapertussis*, *Bordetella ansorpii*, other *Bordetella* species, *Burkholderia mallei*, *Burkholderia psuedomallei*, *Burkholderia cepacian*, *Chlamydia pneumoniae*, *Chlamydia trachomatis*, *Chlamydia psittaci*, *Coxiella burnetii*, *Rickettsial species*, *Ehrlichia species*, *Staphylococcus aureus*, *Staphylococcus aureus* MRSA and MSSA strains, *Staphylococcus epidermidis*, *Streptococcus mutans*, *Streptococcus pneumoniae*, *Streptococcus pyogenes*, *Streptococcus agalactiae*, *Escherichia coli*, *Vibrio cholerae*, *Campylobacter* species, Neiserria meningitidis, Neiserria gonorrhea, *Pseudomonas aeruginosa*, *Pseudomonas aeruginosa* PA14, *Pseudomonas aeruginosa* PAO1, other *Pseudomonas* species, *Haemophilus influenzae*, *Haemophilus ducreyi*, other Hemophilus species, *Clostridium tetani*, other *Clostridium* species, *Yersinia enterolitica*, and other *Yersinia* species, or any combination thereof.

As used herein, "*Mycobacterium tuberculosis*", or "*M. tuberculosis*", refers to a species of pathogenic bacteria in the family Mycobacteriaceae and the causative agent of tuberculosis. *M. tuberculosis* can have a waxy coating on its cell surface due to the presence of mycolic acid, which can make the cells impervious to Gram staining and as a result, can appear weakly Gram-positive. *M. tuberculosis* can infect the lungs and the diagnostic methods to test for *M. tuberculosis* can include tuberculin skin test, acid-fast stain, culture, and polymerase chain reaction.

As used herein, "*Pseudomonas aeruginosa*" refers to an encapsulated, Gram-negative, aerobic, rod-shaped bacterium that can cause disease in plants and animals, including humans. *Pseudomonas aeruginosa* can be associated with serious illnesses, such as hospital-acquired infections like ventilator-associated pneumonia or sepsis syndromes. *Pseudomonas aeruginosa* can also occur during existing diseases or conditions, including cystic fibrosis and traumatic burns. It can aggregate into enduring biofilms and can be capable of extensive colonization.

As used herein, "PA14" refers to one of the three main lineages of *Pseudomonas aeruginosa*. PA14 can be highly virulent and cause disease in a wide range of organisms As used herein, "PAO1" refers to one of the three main lineages of *Pseudomonas aeruginosa*. PAO1 can be moderately virulent and is a chloramphenicol-resistant mutant of the original PAO strain.

As used herein, "*Staphylococcus aureus*" refers to a gram-positive, sphere-shaped bacteria that is the most dangerous of common staphylococcal bacteria. *Staphylococcus aureus* can cause infections including, but not limited to, skin infections, pneumonia, heart valve infections, and bone infections. Infections caused by *Staphylococcus aureus*, often called "staph infections", can include skin infections, often causing abscesses, bloodstream infections, endocarditis, osteomyelitis, and lung infection (pneumonia). Risk factors for a staph infection can include, but are not limited to, influenza, chronic lung disorders, like cystic fibrosis and emphysema, burns, surgery, diabetes mellitus, and chronic kidney disorder.

As used herein, "MRSA", or "methicillin-resistant *Staphylococcus aureus*" refers to a cause of staph infection that is resistant to several antibiotics. MRSA can cause bloodstream infections, pneumonia, surgical site infections, or any combination thereof.

As used herein, "MSSA", or "methicillin-susceptible *Staphylococcus aureus*", refers to a cause of staph infection that can be treated with antibiotics. MSSA can cause skin infections, fever, aches and pains, gastrointestinal symptoms, or any combination thereof.

As used herein, "*Listeria monocytogenes*" refers to a species of pathogenic bacteria that causes the infection listeriosis. *Listeria monocytogenes* is a Gram-positive, non-spor-forming, motile, anaerobic, rod-shaped bacterium. It is a facultative anaerobic bacterium capable of surviving in the presence or absence of oxygen. *Listeria monocytogenes* can grow and reproduce inside the host's cells and can be one of the most virulent foodborne pathogens.

As used herein, "*Mycobacterium smegmatis*" refers to an acid-fast bacterial species in the phylum Actinomycetota and the genus *Mycobacterium*. *Mycobacterium smegmatis* can grow quickly and can be non-pathogenic. In some embodiments, the bacteria can be planktonic cells.

As used herein, "planktonic cells" are free-living or free-swimming bacteria cells in a unicellular life phase. In some embodiments, planktonic cells can disperse and/or colonize new environments. This is in contrast to biofilms, which can allow cells to live in a coordinated, more permanent manner that favors proliferation.

In certain embodiments, the virus can include Herpes Simplex virus-1, Herpes Simplex virus-2, Varicella-Zoster virus, Epstein-Barr virus, Cytomegalovirus, Human Herpes virus-6, Variola virus, Vesicular stomatitis virus, Hepatitis A virus, Hepatitis B virus, Hepatitis C virus, Hepatitis D virus, Hepatitis E virus, Rhinovirus, Coronavirus (such as, for example, avian coronavirus (IBV), porcine epidemic diarrhea virus (PEDV), porcine respiratory coronavirus (PRCV), transmissible gastroenteritis virus (TGEV), feline coronavirus (FCoV), feline infectious peritonitis virus (FIPV), feline enteric coronavirus (FECV), canine coronavirus (CCoV), rabbit coronavirus (RaCoV), mouse hepatitis virus (MHV), rat coronavirus (RCoV), sialodacryadenitis virus of rats (SDAV), bovine coronavirus (BCoV), bovine enterovirus (BEV), porcine coronavirus HKU15 (PorCoV HKU15), Porcine epidemic diarrhea virus (PEDV) porcine hemagglutinating encephalomyelitis virus (HEV), turkey bluecomb coronavirus (TCoV), human coronavirus (HCoV)-229E, HCoV-OC43, HCoV-HKU1, HCoV-NL63, Severe Acute Respiratory Syndrome (SARS)-Coronavirus (CoV) (SARS-CoV), Severe Acute Respiratory Syndrome (SARS)-Coronavirus (CoV)-2 (SARS-CoV-2) (including, but not limited to the B1.351 variant, B.1.1.7 variant, USA-WA1/2020, or P.1 variant), or middle east respiratory syndrome (MERS) coronavirus (CoV) (MERS-CoV)), Influenza virus A, Influenza virus B, Measles virus, Polyomavirus, Human Papillomavirus, Respiratory syncytial virus, Adenovirus, Coxsackie virus, Dengue virus, Mumps virus, Poliovirus, Rabies virus, Rous sarcoma virus, Reovirus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Simian Immunodeficiency virus, Human T-cell Leukemia virus type-1, Hantavirus, Rubella virus, Simian Immunodeficiency virus, Human Immunodeficiency virus type-1, and Human Immunodeficiency virus type-2.

As used herein, "Coronavirus" refers to a species of virus belonging to the subfamily Coronavirinae in the family Coronaviridae, in the order Nidovirales. Coronaviruses are enveloped viruses with a positive-sense single-stranded RNA genome and with a nucleocapsid of helical symmetry.

In one embodiment, the coronavirus infection is an infection of the upper and/or lower respiratory tract. The "upper respiratory tract" includes the mouth, nose, sinus, middle ear, throat, larynx, and trachea. The "lower respiratory tract" includes the bronchial tubes (bronchi) and the lungs (bronchi, bronchioles, and alveoli), as well as the interstitial tissue of the lungs.

In another embodiment, the coronavirus infection is an infection of the gastrointestinal tract. The "gastrointestinal tract" may include any area of the canal from the mouth to the anus, including the mouth, esophagus, stomach, and intestines.

In yet another embodiment, the coronavirus infection is a renal infection.

It is understood and herein contemplated that the coronavirus infections disclosed herein can cause a pathological state associated with the coronavirus infection referred to herein as a "coronavirus disease." In some embodiments, the coronavirus disease is selected from a common cold, pneumonia, pneumonitis, bronchitis, severe acute respiratory syndrome (SARS), coronavirus disease 2019 (COVID-2019), Middle East respiratory syndrome (MERS), sinusitis, porcine diarrhea, porcine epidemic diarrhea, avian infections bronchitis, otitis, and pharyngitis. In some embodiments, the coronavirus infection is a common cold. In some embodiments, the coronavirus infection is selected from SARS, COVID-19, and MERS. In a particular embodiment, the coronavirus infection is COVID-19. In another particular embodiment, the coronavirus infection is IBV, PorCoV HKU15, or PEDV.

Most patients identified with SARS were previously healthy adults aged 25-70 years. A few suspected cases of SARS have been reported among children under 15 years. The case fatality among persons with illness meeting the current World Health Organization case definition for probable and suspected cases of SARS is around 3%.

Other indications associated with coronavirus infections are described in Gralinski & Baric, 2015, *J. Pathol.* 235: 185-195 and Cavanagh, 2005, "Coronaviridae: a review of coronavirus and toroviruses", *Coronaviruses with Special Emphasis on First Insights Concerning SARS* 1, ed. By A. Schmidt, M. H. Wolff and O. Weber, Birkhauser Verlag Baser, Switzerland, each of which is incorporated herein by reference in their entirety.

The coronavirus causing the infection may be selected from an alphacoronavirus, a betacoronavirus, a gammacoronavirus, or a deltacoronavirus.

Representative examples of alphacoronaviruses include, but are not limited to, a colacovirus (e.g., Bat coronavirus CDPHE15), a decacovirus (e.g., Bat coronavirus HKU10, Rhinolophus ferrumequinum alphacoronavirus Hub-2013), a duvinacovirus (e.g., Human coronavirus 229E), a luchacovirus (e.g., Lucheng Rn rat coronavirus), a minacovirus (e.g., Ferret coronavirus, Mink coronavirus 1), a minunacovirus (e.g., Miniopterus bat coronavirus 1, Miniopterus bat coronavirus HKU8), a myotacovirus (e.g., *Myotis rickettii* alphacoronavirus Sax-2011), a nyctacovirus (e.g., *Nyctalus velutinus* alphacoronavirus SC-2013), a pedacovirus (e.g., Porcine epidemic diarrhea virus (PEDV), Scotophilus bat coronavirus 512), a rhinacovirus (e.g., Rhinolophus bat coronavirus HKU2), a setracovirus (e.g., Human coronavirus NL63, NL63-related bat coronavirus strain BtKYNL63-9b), and a tegacovirus (e.g. Alphacoronavirus 1).

Representative examples of betacoronaviruses include, but are not limited to an embecovirus 1 (e.g., Betacoronavirus 1, Human coronavirus OC43, China *Rattus* coronavirus HKU24, Human coronavirus HKU1, Murine coronavirus), a hibecovirus (e.g., Bat Hp-betacoronavirus Zhejiang2013), a merbecovirus (e.g., Hedgehog coronavirus 1, Middle East respiratory syndrome-related coronavirus (MERS-CoV), *Pipistrellus* bat coronavirus HKU5, *Tylonycteris* bat coronavirus HKU4), a nobecovirus (e.g., Rousettus bat coronavirus GCCDC1, Rousettus bat coronavirus HKU9), a sarbecovirus (e.g., severe acute respiratory syndrome coronavirus (SARS-CoV), severe acute respiratory syndrome coronavirus 2 (SARS-CoV-2).

Representative examples of gammacoronaviruses include, but are not limited to, a cegacovirus (e.g., Beluga whale coronavirus SQ1) and an Igacovirus (e.g., Avian coronavirus (IBV)).

Representative examples of deltacoronaviruses include, but are not limited to, an andecovirus (e.g., Wigeon coronavirus HKU20), a buldecovirus (e.g., Bulbul coronavirus HKU11, Porcine coronavirus HKU15 (PorCoV HKU15), Munia coronavirus HKU13, White-eye coronavirus HKU16), a herdecovirus (e.g., Night heron coronavirus HKU19), and a moordecovirus (e.g., Common moorhen coronavirus HKU21).

In some embodiments, the coronavirus is a human coronavirus. Representative examples of human coronaviruses include, but are not limited to, human coronavirus 229E (HCoV-229E), human coronavirus OC43 (HCoV-OC43), human coronavirus HKU1 (HCoV-HKU1), Human coronavirus NL63 (HCoV-NL63), severe acute respiratory syndrome coronavirus (SARS-CoV), severe acute respiratory syndrome coronavirus 2 (SARS-CoV-2), and Middle East respiratory syndrome-related coronavirus (MERS-CoV).

In some embodiments, the coronavirus infection can be caused an avian coronavirus (IBV), porcine coronavirus HKU15 (PorCoV HKU15), Porcine epidemic diarrhea virus (PEDV), HCoV-229E, HCoV-OC43, HCoV-HKU1, HCoV-NL63, SARS-CoV, SARS-CoV-2, or MERS-CoV.

As used herein, "COVID-19" refers to the infectious disease caused by SARS-CoV-2 and characterized by, for example, fever, cough, respiratory symptoms, rhinorrhea, sore throat, malaise, headache, chills, repeated shaking with chills, diarrhea, new loss of smell or taste, muscle pain, or a combination thereof.

In some embodiments, the subject with a coronavirus exhibits one or more symptoms associated with mild COVID-19, moderate COVID-19, mild-to-moderate COVID-19, severe COVID-19 (e.g., critical COVID-19), or exhibits no symptoms associated with COVID-19 (asymptomatic). It should be understood that in reference to the treatment of patients with different COVID-19 disease severity, "asymptomatic" infection refers to patients diagnosed with COVID-19 by a standardized RT-PCR assay that do not present with fever, cough, respiratory symptoms, rhinorrhea, sore throat, malaise, headache, or muscle pain.

In some embodiments, the subject with a coronavirus exhibits one or more symptoms selected from dry cough, shortness of breath, and fever. In other embodiments, the subject exhibits no symptoms associated with COVID-19 but has been exposed to another subject known or suspected of having COVID-19. In further embodiments, the fungi selected from the group can include *Candida albicans, Cryptococcus neoformans, Histoplasma capsulatum, Aspergillus fumigatus, Coccidioides immitis, Paracoccidioides brasiliensis, Blastomyces dermitidis, Pneumocystis carnii, Penicillium marneffi*, and *Alternaria alternata*.

In some embodiments, inhibiting the microorganism can include killing the microorganism.

In certain embodiments, killing the microorganism can include killing bacteria inside a human cell comprising the bacteria.

In further embodiments, ZnPor can be not bactericidal (bacteriostatic). As used herein, "bactericidal" means that a material kills bacteria.

In some embodiments, inhibiting the microorganism can include permeabilizing the microorganism to a material. As used herein, "permeabilize" refers to the puncturing of a cell membrane such that material can enter and exit a cell through the membrane.

In certain embodiments, the ZnPor can be administered at a concentration less than a minimum inhibitory concentration (MIC). As used herein, "minimum inhibitory concentration" or "MIC" refers to the lowest concentration of an antimicrobial that will inhibit the visible growth of a microorganism.

In further embodiments, the material can include DNA, a whole bacteriophage, a partial bacteriophage, an antibiotic, or any combination thereof. As used herein, "antibiotic" refers to a substance that is used to treat and/or prevent bacterial infection by killing bacteria, inhibiting growth of bacteria, or reducing the viability of bacteria.

In some embodiments, permeabilizing the microorganism can include increasing the host range of the bacteriophage. As used herein, "host range" refers to the number of host species used by a pathogen. Host range can reflect the diversity of species that a microorganism can infect. In some embodiments, host range can reflect the diversity of species that viruses can naturally infect. In further embodiments, host range can reflect the range of bacteria a bacteriophage can infect. In certain embodiments, bacteriophage have a narrower host range and can infect only one or a few bacterial strains, while in other embodiments, bacteriophage have a broader host range and can infect many species and possibly even bacteria from different genera.

In certain embodiments, inhibiting the microorganism can include inactivating the bacteriophage. As used herein, "inactivate" refers to eliminating the biological effect of a microorganism. In some embodiments, inactivation of bacteriophage can be accomplished by thermal inactivation, UV or gamma radiation, or addition of peracetic acid, for example. In further embodiments, inactivation of bacteriophage can be caused by ZnPor.

In some embodiments, inhibiting the microorganism can include synergizing the ZnPor (II) with the bacteriophage to inhibit infection caused by bacteria. As used herein, "synergize" refers to the use of ZnPor to increase the size of bacteriophage plaques when the bacteriophage infects bacteria in the presence of sublethal doses of antibiotics. Synergizing can be a component of Phage Antibiotic Synergy (PAS), which can be used in Phage Therapy. Phage therapy is the use of bacteriophages to treat bacterial infections.

In further embodiments, the bacteriophage can include PEV2. As used herein, "PEV2" refers to *Pseudomonas* phage PEV2, which can have a host of *Pseudomonas aeruginosa*.

Method of Treating or Preventing Biofilm Formation of One or More Microorganisms The present disclosure also provides for a method of treating or preventing biofilm formation of one or more microorganisms including contacting the biofilm with zinc porphyrin (ZnPor).

Figures 1A, 1B, 1C, 1D, 1E, 1F:
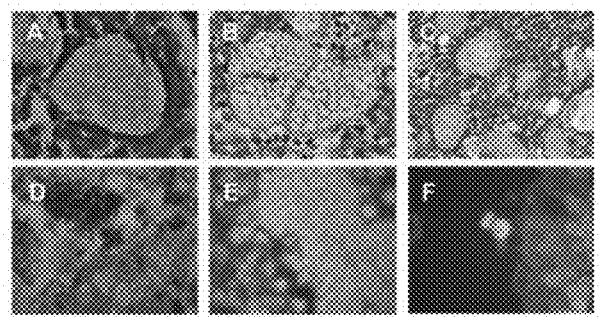
FIGS. 1A-1F show *Pseudomonas aeruginosa* (PsA) biofilm in cystic fibrosis (CF). Psa biofilm in CF airways shown under light microscopy with (FIG. 1A) Gram stain, (FIGS. 1B-1C) H&E stain.

As used herein, "biofilm" refers to surface-associated microbial structures comprising a single microbe (a pure culture), or heterogenous structures comprising different populations of microorganisms, both of which are surrounded by a self-produced matrix that allows for their attachment to animate or inanimate surfaces. In some embodiments, biofilms can be organized communities of bacteria encased in respiratory secretions. (FIG. 1) In further embodiments, biofilms can be associated with clinical bacterial phenotypes predicting clinical deterioration. In addition, PsA biofilms can be associated with the mucoid phenotype, which also predicts clinical deterioration in CF. (Bjarnsholt, T., et al., *Pseudomonas aeruginosa biofilms in the respiratory tract of cystic fibrosis patients*. Pediatr Pulmonol, 2009. 44(6): p. 547-58; Hoiby, N., O. Ciofu, and T. Bjarnsholt, *Pseudomonas aeruginosa biofilms in cystic fibrosis*. Future Microbiol, 2010. 5(11): p. 1663-74; Murray, T. S., M. Egan, and B. I. Kazmierczak, *Pseudomonas aeruginosa chronic colonization in cystic fibrosis patients*. Curr Opin Pediatr, 2007. 19(1): p. 83-8.) Biofilms can include mechanisms of bacterial protection and tissue damage. These can include decreased susceptibility to phagocytosis and strengthened antibiotic resistance due to reduced antibiotic penetration and altered bacterial metabolism. In addition, biofilms can be characterized by continued inflammation, which is dominated by antibody responses and polymorphonuclear leukocytes. Biofilm-associated inflammation can destroy surrounding tissue.

Bacterial biofilms have been found to be up to 1000×more resistant than planktonic cells. A small molecule that could open-up or disassemble the biofilm matrix, would result in greater permeability of the matrix to a wide range of molecules and actions that are highly desirable vis-à-vis treatment of infections. Methods for treating bacterial biofilms are described in, for example, U.S. Pat. No. 8,551,456, which is incorporated herein by reference.

In some embodiments, the biofilm can be caused by a prokaryotic organism. As used herein, a "prokaryotic organism" is a single-celled organism that lacks a nucleus and other membrane-bound organelles.

In certain embodiments, the prokaryotic organism can be selected from the group consisting of *Mycobacterium tuberculosis, Mycobacterium bovis, Mycobacterium bovis* strain BCG, BCG substrains, *Mycobacterium avium, Mycobacterium intracellular, Mycobacterium africanum, Mycobacterium kansasii, Mycobacterium marinum, Mycobacterium ulcerans, Mycobacterium smegmatis, Mycobacterium avium* subspecies paratuberculosis, *Nocardia asteroides*, other *Nocardia* species, *Legionella pneumophila*, other *Legionella* species, *Acetinobacter baumanii, Salmonella typhi, Salmonella enterica*, other *Salmonella* species, *Shigella boydii, Shigella dysenteriae, Shigella sonnei, Shigella flexneri*, other *Shigella* species, *Yersinia pestis, Pasteurella haemolytica, Pasteurella multocida*, other *Pasteurella* species, *Actinobacillus pleuropneumonias, Listeria monocytogenes, Listeria ivanovii, Bacillus subtilis, Brucella abortus*, other *Brucella* species, *Cowdria ruminantium, Borrelia burgdorferi, Bordetella avium, Bordetella pertussis, Bordetella bronchiseptica, Bordetella trematum, Bordetella hinzii, Bordetella pteri, Bordetella parapertussis, Bordetella ansorpii*, other *Bordetella* species, *Burkholderia mallei, Burkholderia psuedomallei, Burkholderia cepacian, Chlamydia pneumoniae, Chlamydia trachomatis, Chlamydia psittaci, Coxiella burnetii, Rickettsial species, Ehrlichia species, Staphylococcus aureus, Staphylococcus aureus* MRSA and MSSA strains, *Staphylococcus epidermidis, Streptococcus mutans, Streptococcus pneumoniae, Streptococcus pyogenes, Streptococcus agalactiae, Escherichia coli, Vibrio cholerae, Campylobacter* species, Neiserria *meningitidis*, Neiserria *gonorrhea, Pseudomonas aeruginosa, Pseudomonas aeruginosa* PA14, *Pseudomonas aeruginosa* PAO1, other *Pseudomonas* species, *Haemophilus influenzae, Haemophilus ducreyi*, other Hemophilus species, *Clostridium tetani*, other *Clostridium* species, *Yersinia enterolitica*, and other *Yersinia* species In further embodiments, the prokaryotic organism can be a Gram positive organism.

In some embodiments, the Gram positive organism can include *Staphylococcus aureus, Streptococcus mutans*, or *Bacillus subtilis*.

In certain embodiments, the biofilm can be caused by a eukaryotic organism. In further embodiments, the eukaryotic organism can include *Candida albicans, Cryptococcus neoformans, Histoplasma capsulatum, Aspergillus fumigatus, Coccidioides immitis, Paracoccidioides brasiliensis, Blastomyces dermitidis, Pneumocystis carnii, Penicillium marneffi*, and *Alternaria alternatas*. As used herein, a "eukaryotic cell" is an organism with cells having a nucleus enclosed within a nuclear envelope. Eukaryotes can reproduce both asexually through mitosis, as well as through meiosis and gamete fusion.

In some embodiments, the biofilm can be caused by prokaryotic organism and a eukaryotic organism.

In certain embodiments, the ZnPor can inhibit one or more virulence factors of the microorganism. As used herein, "virulence factors" refer to the cellular structures, molecules, and regulatory systems that assist bacteria to colonize the host at the cellular level. Virulence factors can be secretory, membrane associated, or cytosolic. Virulence factors can confer the ability to evade host defenses, adhere to cell surfaces, produce toxins and enzymes, display surface structure, or any combination thereof, thereby contributing to pathogenic potential.

In further embodiments, the biofilm can be present on an inanimate surface. In some embodiments, the inanimate surface can include solid surfaces, biomedical devices, titanium joints, dental instruments, catheters, Endotracheal tubes.

In certain embodiments, the biofilm can be present on an animate surface. As used herein, "animate surface" refers to a surface of an active, living organism. In some embodiments, animate surface can include tissue or an organ.

In further embodiments, permeabilizing the biofilm can include disassembling the matrix with ZnPor having a concentration less than a minimum inhibitory concentration.

As used herein, "disassemble" refers to the degradation of the extracellular matrix of a biofilm. In some embodiments, disassembly can include physiological change that prepares cells for conditions outside the biofilm. Disassembly can occur in the presence of specific materials, such as ZnPor.

As used herein, "matrix" refers to the complex array of extracellular polymeric substances that contribute to the unique attributes of a biofilm. A matrix encases the attached microbial cells within the biofilm, surrounding and protecting the cells. In some embodiments, a matrix can include polysaccharides, proteins, lipids, extracellular DNA, or any combination thereof.

In some embodiments, permeabilizing the biofilm can include killing individual microorganism cells, bacterial cells, or bacterial cells in the matrix.

In certain embodiments, the ZnPor can penetrate and disperse within the matrix.

In further embodiments, the biofilm can expand and detach from the animate or inanimate surface.

Method of Treating Disease Associated with Biofilm Formation

The present disclosure also provides for a method of treating a disease associated with biofilm formation in a subject including administering to the subject a composition comprising a therapeutically effective amount of ZnPor.

In some embodiments, the disease can include tooth decay, burn wound infection, ulcers, ventilator associated pneumonia (VAP), cystic fibrosis, pneumonia, medical device associated infection, and chronic wound infections.

In certain embodiments, biofilm can be caused by a microorganisms selected from bacteria, fungi, or viruses, or any combination thereof.

In further embodiments, bacteria can include gram-negative bacteria, gram-positive bacteria, acid-fast bacteria, or any combination thereof.

In some embodiments, bacteria can include *Mycobacterium tuberculosis, Mycobacterium bovis, Mycobacterium bovis* strain BCG, BCG substrains, *Mycobacterium avium, Mycobacterium intracellular, Mycobacterium africanum, Mycobacterium kansasii, Mycobacterium marinum, Mycobacterium ulcerans, Mycobacterium smegmatis, Mycobacterium avium* subspecies paratuberculosis, *Nocardia asteroides*, other *Nocardia* species, *Legionella pneumophila*, other *Legionella* species, *Acetinobacter baumanii, Salmonella typhi, Salmonella enterica*, other *Salmonella* species, *Shigella boydii, Shigella dysenteriae, Shigella sonnei, Shigella flexneri*, other *Shigella* species, *Yersinia pestis, Pasteurella haemolytica, Pasteurella multocida*, other *Pasteurella* species, *Actinobacillus* pleuropneumonias, *Listeria monocytogenes, Listeria ivanovii, Bacillus subtilis, Brucella abortus*, other *Brucella* species, *Cowdria ruminantium, Borrelia burgdorferi, Bordetella avium, Bordetella pertussis, Bordetella bronchiseptica, Bordetella trematum, Bordetella hinzii, Bordetella pteri, Bordetella parapertussis, Bordetella ansorpii*, other *Bordetella* species, *Burkholderia mallei, Burkholderia psuedomallei, Burkholderia cepacian, Chlamydia pneumoniae, Chlamydia trachomatis, Chlamydia psittaci, Coxiella burnetii, Rickettsial* species, *Ehrlichia* species, *Staphylococcus aureus, Staphylococcus aureus* MRSA and MSSA strains, *Staphylococcus epidermidis, Streptococcus mutans, Streptococcus pneumoniae, Streptococcus pyogenes, Streptococcus agalactiae, Escherichia coli, Vibrio cholerae, Campylobacter* species, *Neiserria meningitidis, Neiserria gonorrhea, Pseudomonas aeruginosa, Pseudomonas aeruginosa* PA14, *Pseudomonas aeruginosa* PAO1, other *Pseudomonas* species, *Haemophilus influenzae, Haemophilus ducreyi*, other Hemophilus species, *Clostridium tetani*, other *Clostridium* species, *Yersinia enterolitica*, and other *Yersinia* species or any combination thereof.

In certain embodiments, virus can include Herpes Simplex virus-1, Herpes Simplex virus-2, Varicella-Zoster virus, Epstein-Barr virus, Cytomegalovirus, Human Herpes virus-6, Variola virus, Vesicular stomatitis virus, Hepatitis A virus, Hepatitis B virus, Hepatitis C virus, Hepatitis D virus, Hepatitis E virus, Rhinovirus, Coronavirus (such as, for example, avian coronavirus (IBV), porcine epidemic diarrhea virus (PEDV), porcine respiratory coronavirus (PRCV), transmissible gastroenteritis virus (TGEV), feline coronavirus (FCoV), feline infectious peritonitis virus (FIPV), feline enteric coronavirus (FECV), canine coronavirus (CCoV), rabbit coronavirus (RaCoV), mouse hepatitis virus (MHV), rat coronavirus (RCoV), sialodacryadenitis virus of rats (SDAV), bovine coronavirus (BCoV), bovine enterovirus (BEV), porcine coronavirus HKU15 (PorCoV HKU15), Porcine epidemic diarrhea virus (PEDV), porcine hemagglutinating encephalomyelitis virus (HEV), turkey bluecomb coronavirus (TCoV), human coronavirus (HCoV)-229E, HCoV-OC43, HCoV-HKU1, HCoV-NL63, Severe Acute Respiratory Syndrome (SARS)-Coronavirus (CoV) (SARS-CoV), Severe Acute Respiratory Syndrome (SARS)-Coronavirus (CoV)-2 (SARS-CoV-2) (including, but not limited to the B1.351 variant, B.1.1.7 variant, USA-WA1/2020, or P.1 variant), or middle east respiratory syndrome (MERS) coronavirus (CoV) (MERS-CoV)), Influenza virus A, Influenza virus B, Measles virus, Polyomavirus, Human Papillomavirus, Respiratory syncytial virus, Adenovirus, Coxsackie virus, Dengue virus, Mumps virus, Poliovirus, Rabies virus, Rous sarcoma virus, Reovirus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Simian Immunodeficiency virus, Human T-cell Leukemia virus type-1, Hantavirus, Rubella virus, Simian Immunodeficiency virus, Human Immunodeficiency virus type-1, and Human Immunodeficiency virus type-2.

In further embodiments, fungi can be selected from the group including *Candida albicans, Cryptococcus neoformans, Histoplasma capsulatum, Aspergillus fumigatus, Coccidioides immitis, Paracoccidioides brasiliensis, Blastomyces dermitidis, Pneumocystis carnii, Penicillium marneffi*, and *Alternaria alternata*.

In some embodiments, the method can further include administering to the subject an anti-microbial agent. As used herein, "anti-microbial agent" refers to any of a large variety of chemical compounds and physical agents that are used to destroy microorganisms or prevent their development. Anti-microbial agents can include, but are not limited to, antiseptics, germicides, and antibiotics.

In certain embodiments, the ZnPor can be administered topically. As used herein, "topical" means designed for or involving application to or action on the surface of a part of the body.

In further embodiments, the ZnPor can be formulated in a composition; and wherein the composition can include a cream, salve, lotion, ointment, or spray.

In some embodiments, the method can further include adding bacteriophage, DNA, an extant antibiotic, or any combination thereof. As used herein, "extant antibiotics" are antibiotics that currently exist and have been used clinically but may have lost effectiveness against certain subjects, such as *Mycobacterium tuberculosis*, gram-negative bacterium, or bacterial biofilms. In some embodiments, extant antibiotics can include Tobramycin or Vancomycin.

In certain embodiments, the method can further include light activation.

A number of embodiments of the disclosure have been described. Nevertheless, it will be understood that various modifications may be made without departing from the spirit and scope of the invention. Accordingly, other embodiments are within the scope of the following claims.

By way of non-limiting illustration, examples of certain embodiments of the present disclosure are given below.

EXAMPLES

Example 1: Novel Porphyrin Targets Both *Pseudomonas aeruginosa* and *Staphylococcus Aureus*

Background

Porphyrins Have Diverse Uses in Healthcare. Porphyrins are a class of aromatic, heterocyclic compounds found in nature that play key roles in several organisms (e.g., heme, chlorophyll, cytochromes etc.); and can be artificially synthesized to produce a wide array of variants. (Charnyi, A. M. and S. E. Krasovitskaia, [*Porphyrins*]. Usp Sovrem Biol, 1951. 32(2): p. 166-92; Falk, J. E., Porphyrins. Br Med Bull, 1954. 10(3): p. 211-4; Huang, H., et al., *Emerging applications of porphyrins in photomedicine*. Frontiers in Physics, 2015. 3(23); Huang, X., K. Nakanishi, and N. Berova, *Porphyrins and metalloporphyrins: versatile circular dichroic reporter groups for structural studies*. Chirality, 2000. 12(4): p. 237-55.) Interestingly, porphyrins are one of the earliest recognized classes of DNA ligands. Their interactions with double-stranded DNA (dsDNA) have long been studied, (Fief R J, Howard J C, Mark E H, Datta Gupta N. Interaction of DNA with a porphyrin ligand: evidence for intercalation. Nucleic Acids Res. 1979 Jul. 11; 6(9):3093-118. doi: 10.1093/nar/6.9.3093. PMID: 573891; PMCID: PMC327919) and remain of great interest. Studies have shown that many porphyrins, and their metal derivatives, have high affinity for DNA and bind either by intercalation, external binding, or aggregation, or both. (Yoho, J. et al., Toxicity and localization studies of a potential photodynamic therapy agent in *Drosophila*, 2014; Choi, J. K., A. D'Urso, and M. Balaz, *Chiroptical properties of anionic and cationic porphyrins and metalloporphyrins in complex with left-handed Z-DNA and right-handed B-DNA*. J Inorg Biochem, 2013. 127: p. 1-6.) The extracellular matrix (ECM) of PsA biofilms contains high levels of extracellular DNA (eDNA), which may be a good target for porphyrin molecules. (Chiang, W. C., et al., *Extracellular DNA Shields against Aminoglycosides in Pseudomonas aeruginosa Biofilms*. Antimicrobial Agents and Chemotherapy, 2013. 57(5): p. 2352-2361; Montanaro, L., et al., *Extracellular DNA in Biofilms*. The International Journal of Artificial Organs, 2011.34(9): p. 824-831; Okshevsky, M., V. R. Regina, and R. Meyer, *Extracellular DNA as a target for biofilm control*. Current Opinion in Biotechnology, 2015. 33: p. 73-80.) Disruption of the matrix via porphyrin interactions with eDNA is likely to enhance accessibility by antibiotics and can even result in the detachment of the biofilm from the substrata. An added value in this scenario is that by disrupting eDNA, porphyrins may also disrupt horizontal gene transfer (HGT), an established mechanism that PsA and other bacteria use to pass antibiotic resistance genes to other cells in the biofilm community. (Munita, J. M. and C. A. Arias, *Mechanisms of Antibiotic Resistance*. Microbiology spectrum, 2016. 4(2): p. 10.1128/microbiolspec.VMBF-0016-2015; Salcedo, D. E., et al., *The effects of antibiotics on the biofilm formation and antibiotic resistance gene transfer*. Desalination and Water Treatment, 2015. 54(13): p. 3582-3588; Gula, G., et al., *Complex Signaling Networks Controlling Dynamic Molecular Changes in Pseudomonas aeruginosa Biofilm*. Curr Med Chem, 2019. 26(11): p. 1979-1993; Vorkapic, D., K. Pressler, and S. Schild, *Multifaceted roles of extracellular DNA in bacterial physiology*. Curr Genet, 2016. 62(1): p. 71-9.)

In recent years, there has been increased interest in using light activation of porphyrins to treat bacterial infections. This treatment is referred to as antimicrobial photodynamic therapy (aPDT), which is based on the studies using light activation of porphyrins to treat cancer via PDT. Studies have shown the ability of cationic porphyrins to kill bacterial cells when photoactivated, via production of reactive oxygen species (ROS); Gram-positive (MSSA/MRSA), Gram-negative (PsA, *Escherichia coli*), as well as fungi (*Candida albicans*) are indeed susceptible to light activated porphyrins. Although the results of aPDT are promising using planktonic cells, less is known about efficacy against biofilms. In addition, there are serious limitations in providing light to the site of some of the most serious infections (e.g., PsA biofilm infections in the airway in CF). Such biofilms have a large surface area and are difficult to penetrate with light. Furthermore, the excitation wavelengths of most porphyrins are in the blue light range which may cause tissue damage. Thus, efforts are underway to create porphyrins with excitation wavelengths in the infrared range to overcome this obstacle.

Previous studies have shown that a commercially available porphyrin, known as 5,10,15,20-tetrakis(1-methylpyridino)-21H,23H-porphine, tetra-p-tosylate salt (TMP), is highly effective against PsA biofilms and planktonic cells when photoactivated, while exhibiting little to no toxicity to bacterial cells in the absence of photoactivation. However, it was discovered that when TMP interacted with PsA biofilms it could cause disruption and detachment from the substrata without light activation. It was also discovered that TMP could render the biofilm-associated cells of PsA sensitive to tobramycin, gentamycin, and vancomycin; light activation was not required. To determine whether eDNA in the ECM was the target of TMP, the effect of TMP on a wild-type PsA strain and a mutant (pqsA) strain that has little to no eDNA production in biofilms was tested. In these experiments, TMP was shown to have no effect on the pqsA mutant biofilms.

Figure 3:
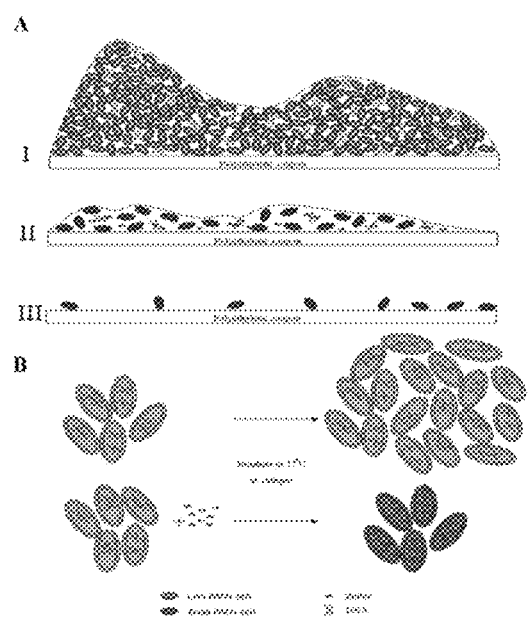
FIG. 3 shows a proposed model of the mechanism of action of ZnPor (II) against PsA biofilms and individual cells.
Figure 4:
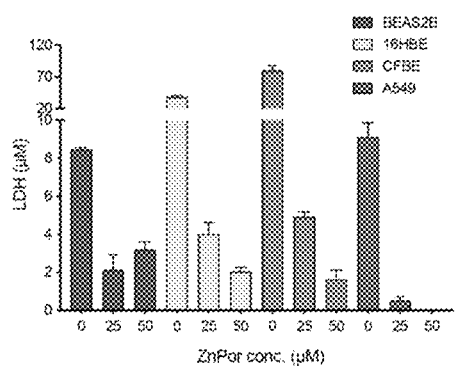
FIG. 4 shows the effects of ZnPor on lactate dehydrogenase (LDH) production in pulmonary cell lines. Representative of one experiment.

A Novel Zinc Porphyrin Shows Activity against PsA and SA. A porphyrin was identified that can disrupt the biofilm matrix, as observed with TMP, and directly kill bacteria without photoactivation. After screening numerous existing porphyrins, with none having the desired activities, a porphyrin was constructed. (Robinson and Swavey. 2014. U.S. Pat. No. 9,364,537; 20). This porphyrin, designated as ZnPor (5,10,15-tris (N-methyl pyridyl)-20-pentafluorophenyl porphyrinatozincTris-4-methylbenzenesulfonate), was a cationic, metallo-porphyrin with Zinc as the central metal ion. ZnPor has a direct antibacterial activity against PsA planktonic and biofilm-associated cells, as well as the ability to dissociate its biofilm matrix, both in the presence and absence of light via a unique mechanism of action (FIG. 3). ((Patel, N et al., A Cationic Porphyrin, ZnPor, Disassembles *Pseudomonas aeruginosa* Biofilm Matrix, Kills Cells Directly, and Enhances Antibiotic Activity of Tobramycin, 2020.) ZnPor also has activity against MSSA/MRSA.

Based on development of ZnPor and the problem of PsA and MSSA/MRSA infection in CF, ZnPor has high potential to fill a need in medical treatment in CF. Specifically, ZnPor has bactericidal activity against key Gram-positive (SA) and Gram-negative (PsA) organisms and is able to disrupt bacterial biofilm, all important components to successful antimicrobial functions in the CF airway milieu. Thus, the use of ZnPor in treating PsA and MSSA/MRSA infections in CF was further investigated. The experiments utilized clinical CF isolates of PsA and MSSA/MRSA and test efficacy and safety of ZnPor in vitro against these isolates, as well as against PsA pulmonary infection in mouse models of CF.

Potential Importance of the Proposed Work to CF. Pulmonary disease is the leading cause of morbidity and mortality in CF, and infection is one of the major drivers of pulmonary disease in CF. (Zemanick, et al., *Cystic Fibrosis: Microbiology and Host Response*, 2016.) PsA and SA (MSSA/MRSA) are highly prevalent organisms in CF infection, are associated with increased morbidity/mortality, and can form biofilms, making their eradication difficult. Despite this, antibiotics and treatment strategies for PsA and SA are limited. A Delphi process of CF experts established treatment strategies for PsA in CF as one of the top ten research priorities in CF. (Rowbotham, New Jersey, et al., *The top 10 research priorities in cystic fibrosis developed by a partnership between people with CF and healthcare providers*. Thorax, 2018.) ZnPor, a novel porphyrin molecule, treated both PsA and SA infection in CF and showed minimal pulmonary cell toxicity. This example tested efficacy and safety of ZnPor against CF isolates of PsA and SA in CF airway epithelial cells and against PsA in animal models of CF infection. These findings advance development of this novel molecule in the treatment of PsA and SA infection in CF.

Goals

The first goal was to investigate the efficacy and safety of ZnPor in PsA infection, and more specifically to examine anti-Pseudomonal activity of ZnPor both in vitro and in vivo and to investigate potential toxicity of ZnPor during treatment of PsA infection. ZnPor activity against PsA isolated from CF patients was tested in vitro in CF airway epithelium. The capacity of ZnPor to decrease infection and enhance survival in vivo in PsA pneumonia was investigated. Initial experiments established efficacy in wildtype (WT) mice, and subsequently CF mice were used. In vitro experiments examined cellular toxicity in human CF airway epithelial cells with ZnPor application. Cell death pathway analysis was performed. In vivo experiments evaluated pulmonary and systemic toxicity of ZnPor therapy in PsA pneumonia.

The second goal is to examine antimicrobial activity of ZnPor against MSSA and MRSA infection in vitro. The ability of ZnPor to eradicate MSSA and MRSA isolates from CF patients in vitro can be tested using CF airway epithelial cells. Toxicity against CF airway epithelial cells can be assessed via a multimodal analysis.

The third goal is to evaluate ZnPor activity against PsA, SA, and polymicrobial biofilm. The ability of ZnPor to eradicate bacterial biofilm can be assessed in vitro. PsA and SA biofilm models can be deployed, including usage of bacteria with a bioluminescent reporter system. In addition, ZnPor activity against a polymicrobial biofilm model using both PsA and SA can be tested.

Results

Figures 2A, 2B, 2C:
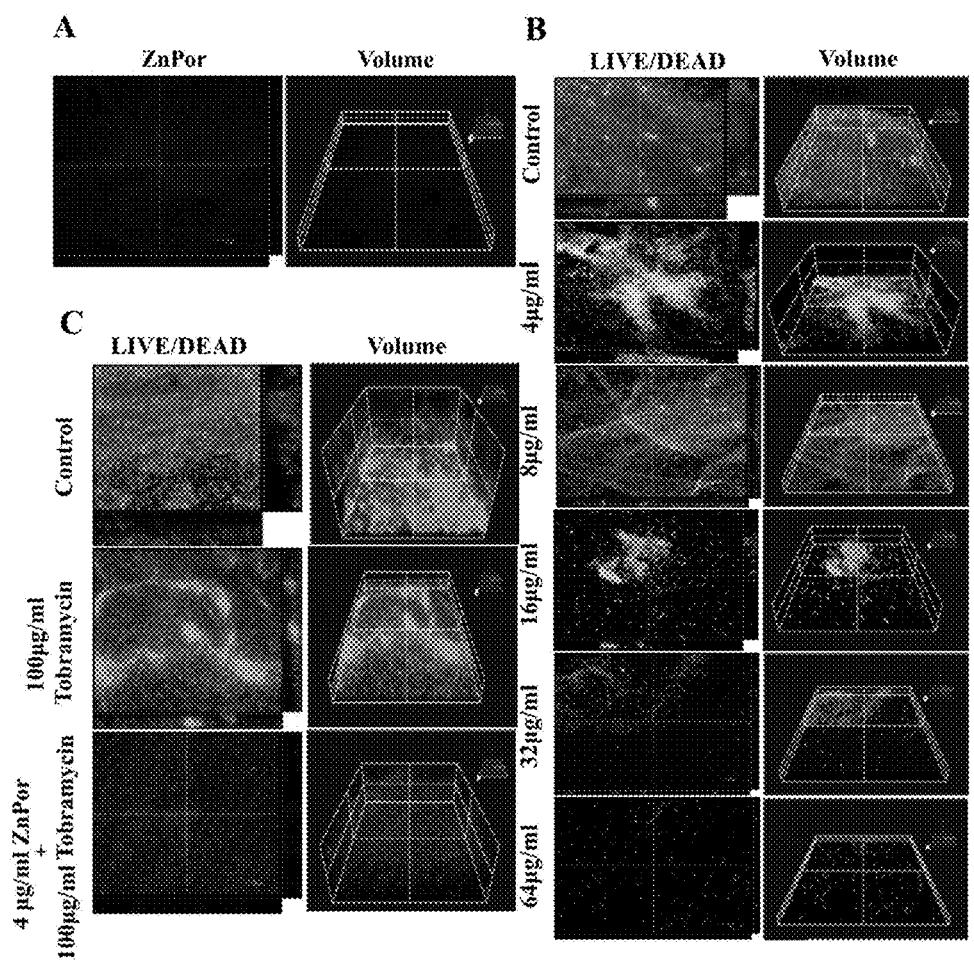
FIGS. 2A-2C show the distribution and effect of ZnPor against PsA PAO1 biofilm. These experiments use confocal microscopy to image PsA biofilms formed on polyethylene coupons in CDC approved bioreactors for 16-18 h.

ZnPor showed activity against PsA, MSSA/MRSA, and biofilm in vitro. Biofilm formation was an important defense mechanism utilized by bacteria and was associated with bacterial phenotypes that predict worse clinical outcomes in CF. A biofilm model was deployed using an SA strain with genetically embedded bioluminescence reporter to gauge efficacy of ZnPor against SA biofilm. Plastic plates were coated with bioluminescent SA and treated with escalating doses of ZnPor or PBS. Bioluminescence was measured via spectrophotometer. ZnPor treatment resulted in significantly less biofilm formation as measured via this technique (FIGS. 2A-2C).

ZnPor showed minimal toxicity in CF airway epithelial cells. Based on bactericidal activity of ZnPor, ZnPor was tested to determine whether it showed toxicity against human pulmonary cells. Human airway epithelial (BEAS2B, 16HBE, CFBE) and alveolar epithelial (A549) cells were cultured, plated on 12-well plates, serum starved overnight, and treated with increasing doses of ZnPor. Cell culture supernatants were collected after 48 h of treatment, and supernatants were then assayed for lactate dehydrogenase (LDH), a general marker of cell death released into the supernatant after cell lysis. Treatment with ZnPor resulted in significantly less LDH in the cell culture supernatant than treatment without ZnPor (negative control). A dose response of decreased LDH for increased dose of ZnPor was seen in 16HBE, CFBE, and A549 cells. These data support that ZnPor application results in minimal cell death in human airway and alveolar epithelial cells.

Figure 5:
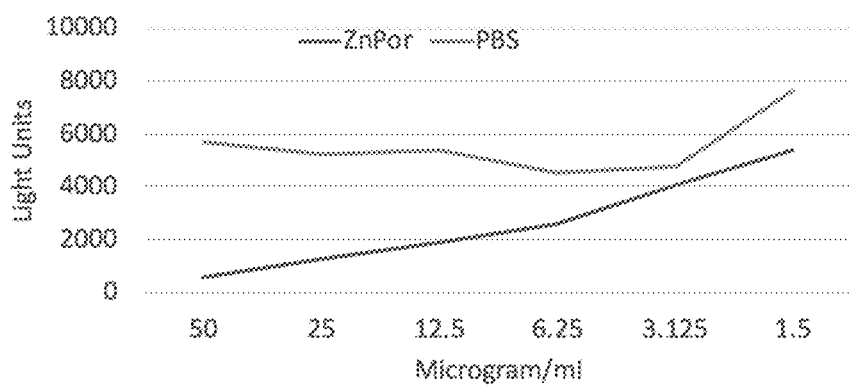
FIG. 5 shows the effect of ZnPor on SA biofilm measured by bioluminescence. Representative of one experiment.

ZnPor showed activity against PsA in mouse model of PsA infection. Based on in vitro experiments showing significant bactericidal activity of ZnPor against PsA and minimal toxicity of ZnPor in vitro in airway and alveolar epithelial cells as well as in monocytes/macrophages, the next experiments examined efficacy and safety of ZnPor in PsA infection in mice. Wildtype (WT) mice were anesthetized and infected with $5 \times 10^6$ CFU PsA via intratracheal route. Immediately following infection, mice were anesthetized again and treated with ZnPor (125 µM) or PBS (negative control). Mice were monitored for clinical signs of toxicity. At 16 h, mice were sacrificed and bronchoalveolar lavage (BAL) and lungs were isolated. Bacterial titers were measured in BAL and lung homogenates in ZnPor-treated versus untreated (negative control) mice, and ZnPor treatment resulted in significantly decreased PsA infection compared with no treatment (FIG. 5). No clinical toxicity was observed in ZnPor-treated versus untreated mice. These data support that ZnPor is able to effectively eradicate acute PsA lung infection in vivo and exhibits minimal clinical toxicity.

Experimental Design and Methods

1. In Vitro Experiments Testing Efficacy and Toxicity of ZnPor Against CF Isolates of PsA and MSSA/MRSA.

Figures 6, 7:
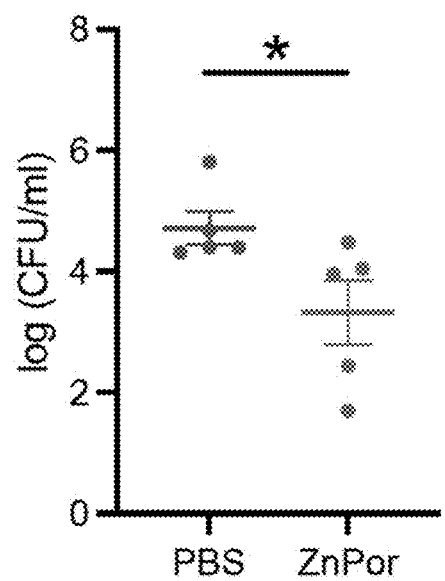
FIG. 6 shows the effects of ZnPor treatment were assessed in wildtype mice infected with PsA. Mice were infected with PsA intratracheally, and subsequently treated with 125 μM ZnPor intratracheally. Bronchoalveolar lavage (BAL) was collected at 16 h. Bacterial titers were measured in BAL. *$p<0.05$, Mann-Whitney U. Representative of one experiment.
FIG. 7 shows the exemplary cell lines used in proposed in vitro experiments.
Figures 10A, 10B:
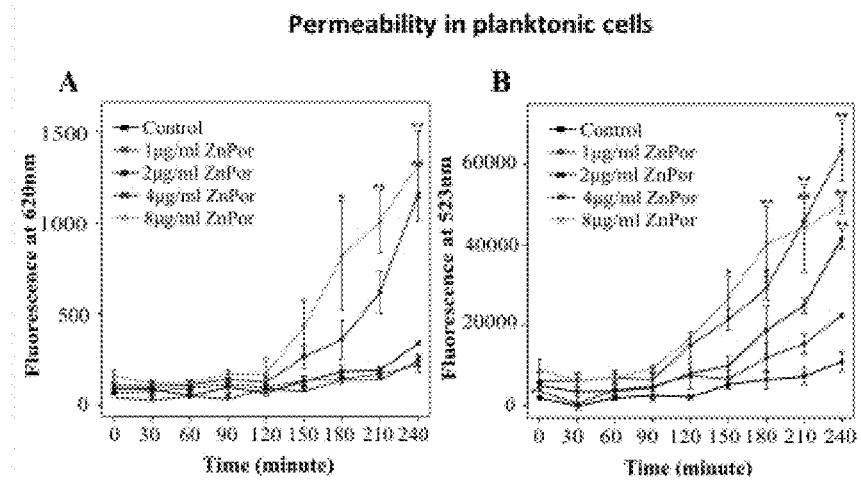
FIGS. 10A-10B show the effect of ZnPor (II) on planktonic cells of PsA.
Figures 11A, 11B:
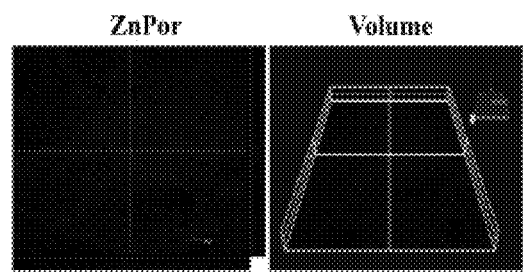
FIGS. 11A-11B show the penetration of ZnPor (II) into the biofilm matrix of PsA.
Figures 12A, 12B:
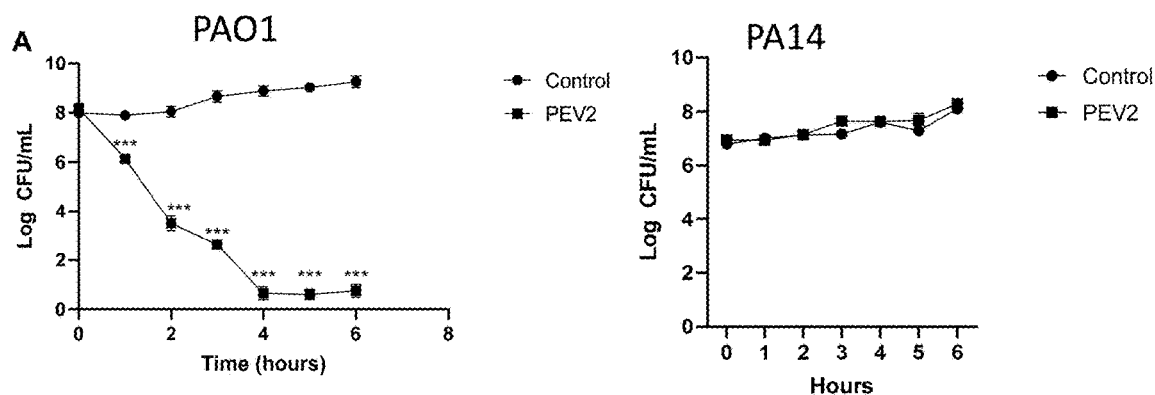
FIGS. 12A-12B show the time kill curves of phage PEV2 (MOI 10:1) against PAO1 (FIG. 13A) and PA14 (FIG. 13B) strains of PsA. Overnight cultures of strains PAO1 and PA14 grown in MSG were diluted in fresh MSG media to $10^6$ cells/mL. Phage PEV2 was added (10:1 MOI) and tubes were shaken aerobically for 6 hours. Control treatments were not treated with PEV2. Viable cell counts were determined by serially diluting bacterial cells onto a LB agar plate at each timepoint. Data from 3 separate experiments represents total mean±standard error, total (n=15) and (n=12) respectively.
Figures 13A, 13B:
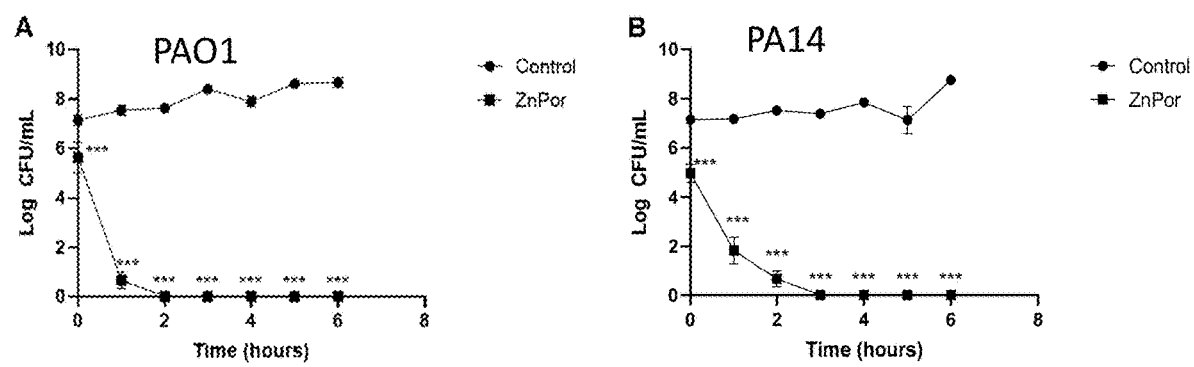
FIGS. 13A-13B show the time kill curve of ZnPor (II) (25 μg/mL) against PAO1 (FIG. 12A) and PA14 (FIG. 12B) strains of PsA. Overnight cultures of strain PAO1 and PA14 grown in MSG media were diluted in fresh MSG to $10^6$ cells/mL with fresh medium. ZnPor was added (25 μg/ml) and cultures were grown aerobically, with shaking, for 6 hours. Viable cell count (CFU per ml) was determined by serially diluting bacterial cells at the indicated time points, onto LB agar. Data from 3 separate experiments represents total mean±standard error, total (n=9) and (n=8) respectively.

These experiments can evaluate the efficacy and safety of ZnPor in PsA and SA infection in human CF airway epithelial cells. The cell lines used are outlined in FIG. 7. CF pathogens [e.g., PsA and SA (MSSA and MRSA)] were provided by Yale's Center for Phage Biology & Therapy. PsA and SA were cultured from sputum samples and biobanked. This Center will continue to provide deidentified clinical isolates from CF subjects that have provided sputum.

Protocols: Cells can be infected with isolates of PsA. At first, experiments can be done in non-CF airway epithelial cells, and subsequently experiments can be repeated in CF airway epithelial cells (e.g., CFBE). A total of 20 CF PsA isolates can be tested. Cells can be treated with ZnPor at increasing concentrations. After a predetermined time point, infection can be quantified based on bacterial titer.

Data expected, means of analysis/interpretation: For evaluation of efficacy, quantification of bactericidal activity (e.g., bacterial titers) can be performed, and treated versus untreated cells can be compared. A total of 3 cell samples can be tested per isolate for each group (3 ZnPor treated, 3 untreated, or n=3) in order to calculate statistical significance.

2. Evaluation of ZnPor Toxicity in PsA and SA Infection in Human CF Epithelial Cells.

Evaluation of toxicity can be completed by performing a cell death pathway analysis on treated and untreated cells. Here, the rationale tested is that early detection of ZnPor toxicity in epithelial cells can be detected with high sensitivity. At first, we can evaluate toxicity of ZnPor treatment alone versus no treatment. Subsequently, we can evaluate toxicity of ZnPor treatment of PsA versus PsA infection alone to determine effect of concomitant infection on ZnPor toxicity. A total of at least 3 samples can be treated per group (3 ZnPor treated, 3 untreated, or n=3) to calculate statistical significance. Cell death pathway analysis can include techniques outlined in FIG. 8.

First, we can measure lactate dehydrogenase (LDH) in cell culture supernatants after ZnPor treatment. This can provide a general estimate of cell death. We can perform TUNEL staining, a general marker of cell death and/or apoptosis, on treated cells and visualized labeling using IF, which can provide a quantitative measurement of cell death and allow direct comparison of treated versus untreated cells. LDH and TUNEL assays can be used as screening techniques. If there is a significant signal of cellular toxicity, then a more detailed cell death analysis can be pursued to further decipher the mechanism of cell death. This further analysis can include flow cytometry with Annexin V/propidium iodide (PI) labeling to identify early versus late cell death/apoptosis, measurement of caspase activity to differentiate apoptotic pathways, and protein measurement via Western blot for apoptotic/anti-apoptotic proteins, as well as proteins shared by intrinsic and extrinsic apoptotic pathways.

3. In Vivo Experiments Testing Efficacy and Safety of ZnPor Against PsA in Mouse Model.

Mouse genetics: For animal experiments, we can utilize wildtype (WT) mice, gut-corrected CF mice, and ENaC-overexpressing mice. Experiments can be first completed using WT mice. Then, gut-corrected CF mice and ENaC-overexpressing mice can be used. For infection experiments, 6-8 mice per group (6 ZnPor-treated, 6 PBS-treated) can be used, and both male and female mice can be used at equal proportions. All experiments can be done in triplicate (n=3).

PsA isolates: Initial in vivo experiments can utilize WT PsA (e.g., strain PAO1). Subsequently, clinical CF isolates of PsA can be used for animal infection. CF pathogens [e.g., PsA and SA (MSSA and MRSA)] can be provided by Yale's Center for Phage Biology & Therapy. PsA and SA can be cultured from sputum samples and biobanked.

Protocols: For pulmonary PsA infection in mice, first PsA can be cultured overnight. Using a spectrophotometer, the bacterial load can be calculated in the specimen that was cultured overnight at different dilutions. A final concentration of $1 \times 10^8$ CFU/ml can be determined and prepared. PsA can be resuspended in PBS, and the final bacterial amount can be $5 \times 10^7$ CFU/ml. Mice can be anesthetized, and 50 μl of this solution (total bacteria=$2.5 \times 10^6$ CFU per mouse) can be administered intratracheally through the mouth. Mice can be allowed to recover, anesthesia can be completed again (15 minutes of elapsed time since infection), and mice can be treated with 50 μl of ZnPor (concentration=250 μg/ml) or PBS (negative control) intratracheally through the mouth. After 16 h, mice are sacrificed, and BAL and lungs are collected for analysis. BAL and lungs can be processed for microbiologic analysis and measurement of acute lung injury.

Survival experiments can also be performed. For these experiments, mice are infected with PsA as above and treated with ZnPor or PBS (negative control) and are monitored for survival. If clinical signs of severe infection indicating a moribund state are present, the mouse is euthanized based on the IACUC protocol. The mice are monitored every 1 h for survival.

Toxicity experiments can also be performed. For these experiments, mice are treated with ZnPor alone or PBS (negative control). Mice are not infected so as to isolate any toxic effects of treatment. Mice are monitored clinically every 2 h for any signs of toxicity. At pre-determined time points, mice are sacrificed, and BAL and lungs are collected for analysis. Blood and bones are also collected for testing of hematopoiesis toxicity. Time points included 16 h, 24 h, 48 h, 1 week, and 2 weeks. The rationale is to sufficiently examine possible toxicity remote from treatment.

Data Expected, Means of Analysis/Interpretation

Evaluation of infection and acute lung injury: Infection can be evaluated by measuring bacterial titers in BAL and lung homogenates. BAL is plated on pre-prepared bacterial culture plates, and the plates are incubated overnight. Bacterial colony counts are then performed, and final bacterial amount is calculated. Bacterial titers are compared between ZnPor-treated and PBS-treated (negative control) mice. For statistical analysis, Mann-Whitney U test can be used to compare data between groups. A significant decrease in bacterial amount with ZnPor treatment can be interpreted as proof of efficacy.

In addition, we can analyze acute lung injury in ZnPor-treated versus PBS-treated groups (FIG. 9). For each of these metrics, ZnPor-treated versus untreated (PBS) groups are evaluated and compared. For statistical analysis, Mann-Whitney U test can be used to compare data between groups. A significant decrease in total cell count, total protein, and LDH is interpreted as proof of reduction in acute lung injury (ALI). A significant decrease in neutrophils by cell differential is interpreted as proof of reduction of innate immune activation. For histopathology, standard scoring for inflammation can be used, and a decrease in score is interpreted as decreased inflammation.

Survival measurement: ZnPor-treated versus untreated (PBS negative control) mice for survival in PsA infection can be evaluated and compared. Kaplan-Meyer curves can be generated. For statistical analysis, log-rank test can be performed.

Toxicity analysis: Toxicity studies can evaluate for presence of lung toxicity, systemic toxicity, as well as hematopoietic and additional system toxicity. BAL and lung homogenates are tested for acute lung injury as in the infection studies (FIG. 9). If toxicity is identified, levels of key inflammatory cytokines are measured to investigate inflammatory pathways that are activated by ZnPor, including IL-1a, IL-1b, IL-6, IL-8, IL-12, IFN-gamma, MCP-1, MIP-1a, MIP-1b, TNF-alpha, as well as others. For each of these metrics, ZnPor-treated versus untreated (PBS) groups can be evaluated and compared. For statistical analysis, Mann-Whitney U test can be used to compare data between groups. A significant increase in total cell count, total protein, and LDH can be interpreted as increased ALI and, hence, toxicity. A significant increase in neutrophils by cell differential can be interpreted as proof of heightened innate immune activation. For histopathology, we can use standard scoring for inflammation, and increase in score is interpreted as heightened inflammation and, hence, toxicity.

In addition to lung inflammation and innate immune activation, systemic and other forms of toxicity pertinent to ZnPor treatment can be monitored and measured. Hematopoietic toxicity with zinc porphyrin treatment has been described. (Lutton, J. D., et al., *Zinc porphyrins: potent inhibitors of hematopoiesis in animal and human bone marrow*. Proc Natl Acad Sci USA, 1997. 94(4): p. 1432-6.) Complete blood counts (CBC) on blood samples are completed, including white blood cell counts with cell differential counts. CBCs can be evaluated and compared amongst and between treated and controls. For statistical analysis, Mann-Whitney U test can be used to compare data between groups. A significant decrease in hemoglobin, hematocrit, platelets, white blood cells, neutrophils (polymorphonuclear lymphocyte), and lymphocytes is interpreted as a possible hematopoietic effect by ZnPor. In addition, peripheral blood smears are completed and analyzed by light microscopy for evidence of reduced hematopoiesis. Bones can be processed for histopathology, and bone marrow can be analyzed for evidence of reduced hematopoiesis. Scores for hematopoiesis are generated for peripheral blood and bone marrow, and scores are evaluated and compared between treated (ZnPor) and untreated (control) mice.

Example 2: ZnPor (II) is a First in Class and has a Novel Target as an Anti-Infective There is empirical evidence that porphyrins do not kill healthy cells unless photoactivated before they have time to break the porphyrin ring and degrade the rest of the molecule. Cancer cells and bacteria constantly replicate, made possible by DNA not bound with Histones. Porphyrins do not appear to be able to bind to DNA bound by histones, such as in healthy mammalian cells.

There is interest in aPDT (antimicrobial Photodynamic Therapy). Bacteria was exposed to the porphyrin followed by photoactivation at 422 nm light (300 W). This resulted in the production of ROSs, if oxygen was present; resulting in the destruction of many major macromolecules (NA, proteins, lipids etc.) leading to cell death. However, many porphyrins are not water soluble and presented problems with uptake into bacterial cells. ZnPor (II) is water soluble and highly effective at killing a broad range of bacteria, and select viruses, without photoactivation.

Figure 14:
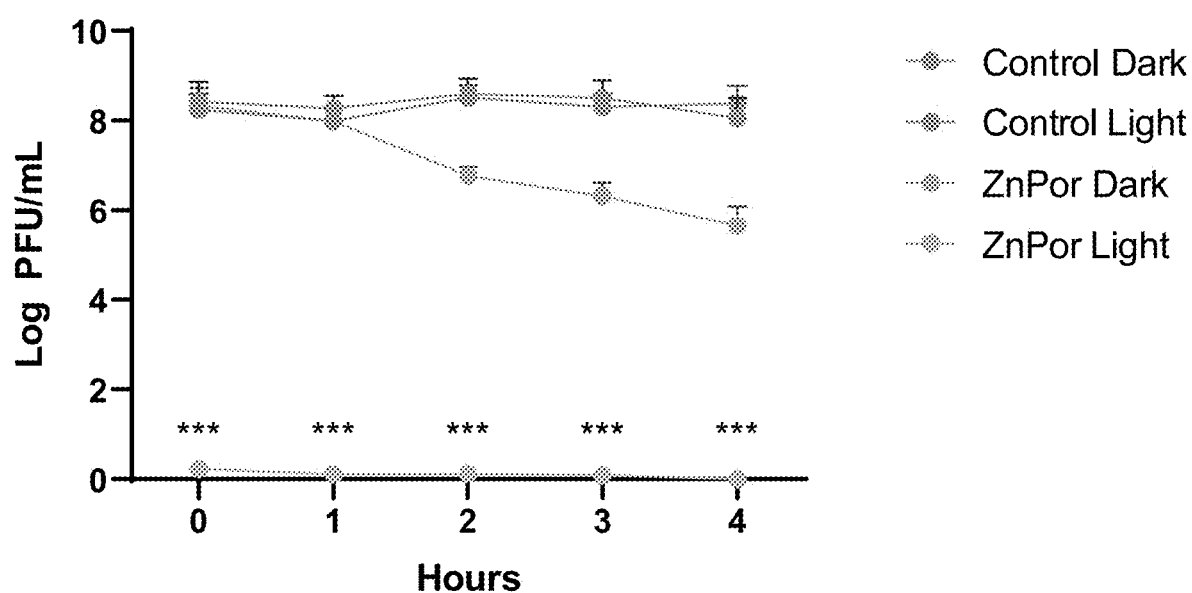
FIG. 14 shows the effects of ZnPor (II) against phage PEV2 with and without photoactivation. Phage PEV2 was diluted to $10^9$ PFU/mL in phage buffer and treated with ZnPor (25 μg/mL) for a total of 4 hours. A 300 W light was used to photoactivate ZnPor_light treatments for 20 minutes. Measurements of plaque forming units (PFU/mL) were taken at each timepoint by serially diluting phage to determine titer using a soft agar overlay protocol. Data from 3 separate experiments represents total mean±standard error, total (n=8).
Figures 16, 17:
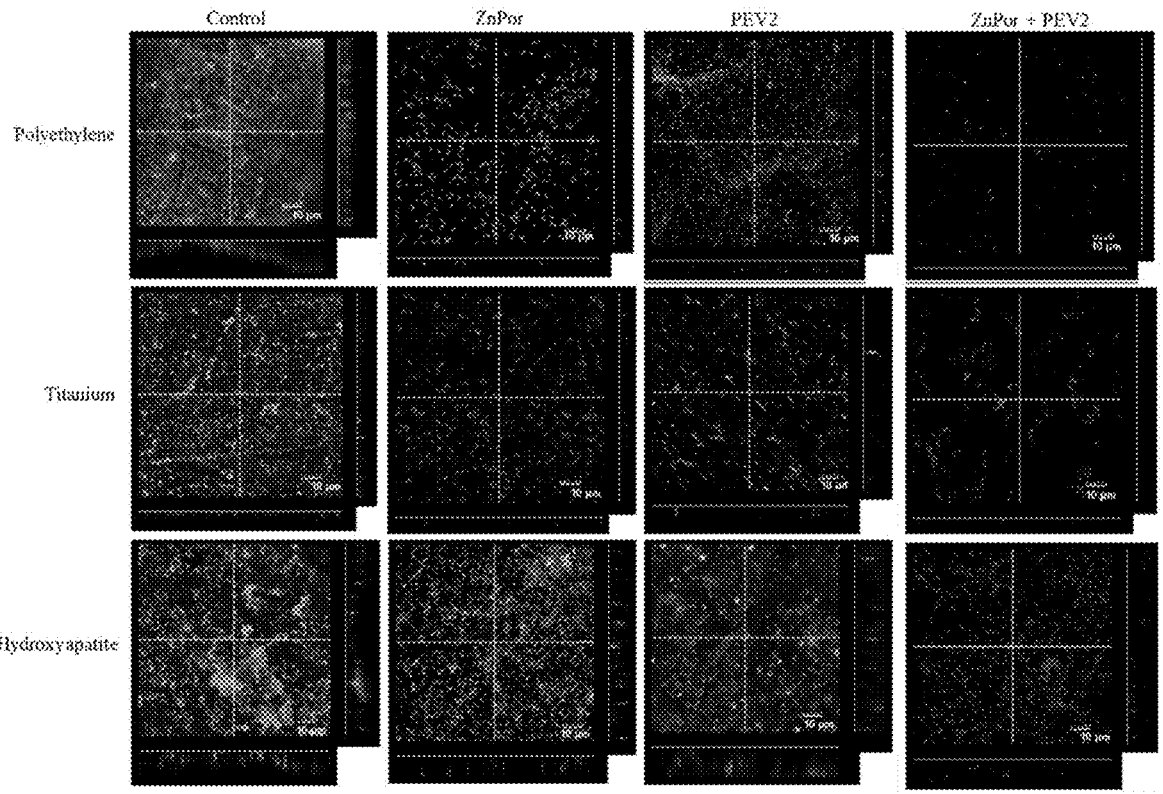
FIG. 16 shows exemplary treatment of Pseudomonas aeruginosa PAO1 biofilms with ZnPor (II) or in combination with phage PEV2 on biomedically relevant substrata. Confocal microscopy was used to image biofilms grown on coupons of various substrata in CDC approved bioreactors (BioSurface Technologies Corp.) Biofilms of strain PAO1 were grown on coupons of the materials shown in MSG media for ~16-18 hours. Overnight media was replaced with PBS and biofilms were treated with either: 1) ZnPor (II) at 25 μg/mL only; incubated for 2 hours; 2) infected with phage PEV2 (MOI of 10:1) for 4 hours or 3) treated with ZnPor (25 μg/mL) for 2 hours followed by the addition of PEV2 (MOI of 10:1) for additional 4 hours. Coupons were gently washed in distilled water and were treated with LIVE/DEAD™ stain. All coupons were imaged using confocal laser scanning electron microscopy (CLSM) at 60×. Green=LIVE Red=DEAD. Control refers to a biofilm that received no treatment. Pictures are representative of total treatments.
Figures 18A, 18B, 18C, 18D, 18E, 18F:
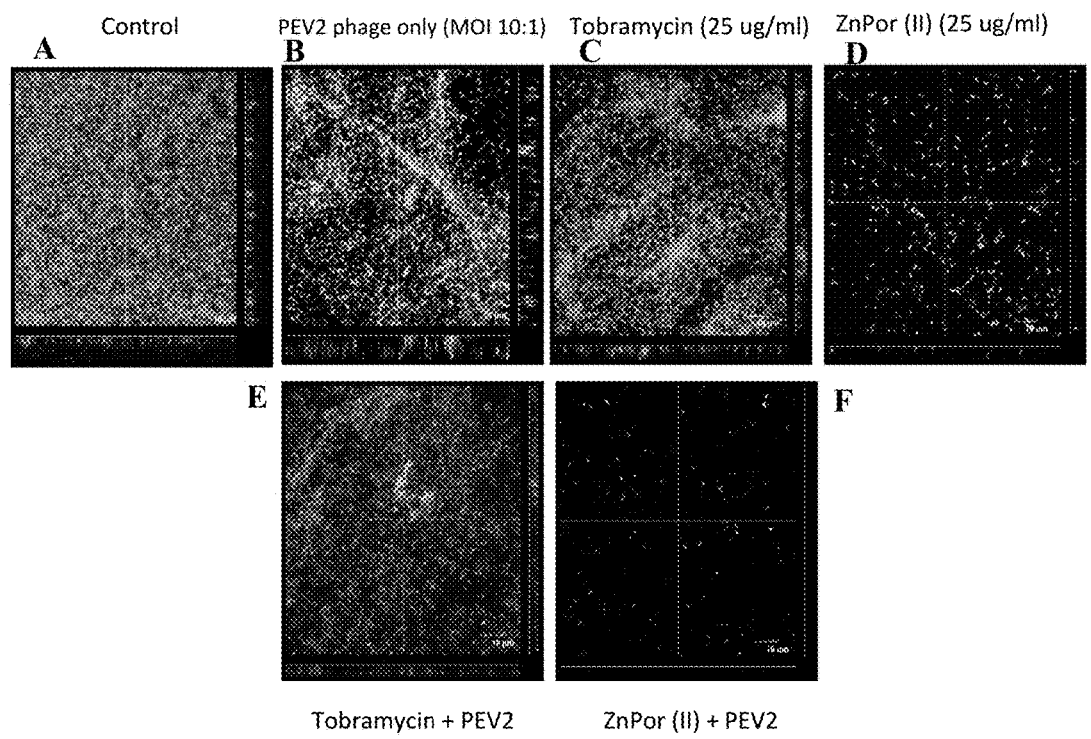
FIGS. 18A-18F show comparison of ZnPor (II) vs. Tobramycin used in combination with phage PEV2 against biofilms of strain PAO1. Biofilms were grown on polyethylene coupons in CDC approved bioreactors in MSG media for ~16-18 hours. Overnight media was replaced with PBS and biofilms were treated with either, ZnPor (II) or Tobramycin at (25 μg/mL) and incubated for 2 hours. Phage PEV2 (MOI of 10:1) were added following the 2 h pretreatment with ZnPor (II) or Tobramycin. At the end of the 2 h Phage PEV2 was added to achiever an MOI of 10:1 and incubated for 4 hours. Coupons were gently washed in distilled water and were treated with LIVE/DEAD™ stain. All coupons were imaged using confocal laser scanning electron microscopy (CLSM) at 60×. Green=LIVE Red=DEAD. Control refers to a biofilm that received no treatment.
Figures 19A, 19B, 19C, 19D:
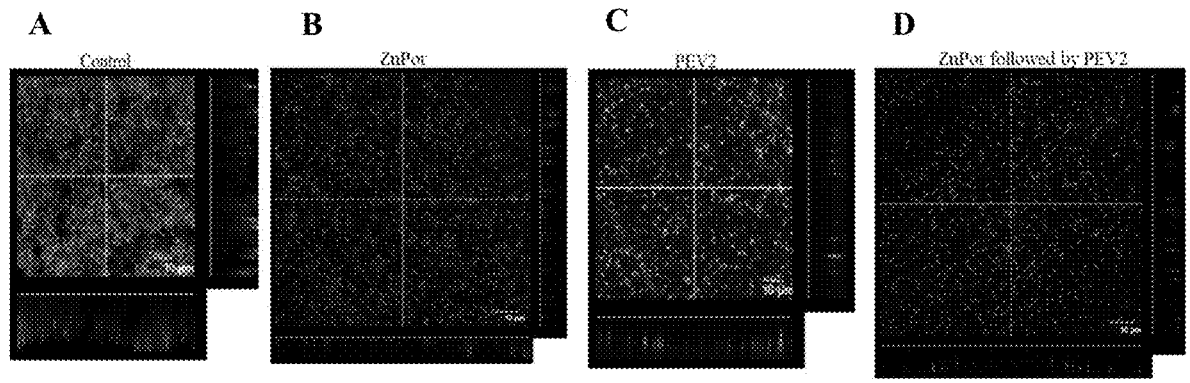
FIGS. 19A-19D shows treatment of PsA PA14 biofilms with PEV2. Biofilms were grown on polyethylene coupons in CDC approved bioreactors in MSG media for ~16-18 hours. Overnight media was replaced with PBS and biofilms were treated as follows.

ZnPor (II) is the only porphyrin that kills Gram-positive and Gram-negative bacteria without photoactivation. It is also effective at killing the acid fast bacterium *Mycobacterium tuberculosis*. Additionally, ZnPor (II) inactivates the bacteriophage PEV2, a well-studied bacteriophage of *Pseudomonas aeruginosa*. PEV2 is currently being used in phage therapy in Europe. And ZnPor (II) retains the ability to be photoactivated which results in quicker and greater killing—see FIG. 14 to see the difference in ZnPor (II) with and without photoactivation against PEV2 bacteriophage. While ZnPor (II) can inactivate phage, at lower concentrations it can act synergistically with bacteriophage PEV2 or the purified genome of PEV2 in remediation of biofilms of PsA. This is referred to as PAS Phage Antibiotic Synergy (PAS) and is of great interest and intense study; as a means to overcome several known limitations of phage-only "Phage Therapy".

Example 3: Testing for Bacterial Resistance

One of the major concerns of developing novel small molecule antimicrobials is the potential for bacteria to develop resistance. No colony growth was observed on LB plates from 2×, 4× and 8×MIC concentration of ZnPor with PsA cell. These tests were repeated, and no resistance was observed against ZnPor (II) at any time during 8 years of testing. The mechanism of action and target are believed to explain the absence of resistance. An MBC:MIC ratio of 2 which is what we derived from kill curves, was considered an indication of lack of resistance.

There was no toxicity to human lung or skin cells grown in tissue culture at levels up to times greater than the concentration required to kill PsA bacteria, over 100 times greater than the MBC for *S. aureus* MRSA strain. Additionally, ZnPor (II) is not toxic to *Drosophila*. Flies were fed ZnPor (II) and tested for toxicity, fecundity etc. (Yoho, J. et al., Toxicity and localization studies of a potential photodynamic therapy agent in *Drosophila*, 2014).

Example 4: Permeating Bacterial Cells with ZnPor (II)

The preincubation of planktonic PsA PAO1 cells with ZnPor (II) (FIGS. 10A-10B and 11A-11B) allowed the impermeant dye Syber Green™ to get into the cells in a dose response manner; it did not get into untreated cells. Syber Green™ can pass through the cell wall into PsA cells pre-treated with ZnPor (II) at concentrations as low as 1 µg/mL; this is below the MIC (4 ug/m). Cells treated with ZnPor (II) allowed the entry of the Syber Green molecule even at sub-MIC concentrations of ZnPor (II).

ZnPor (II) permeabilized the cell wall of *Pseudomonas aeruginosa* cells and accumulated in the cytoplasm. (Patel, N et al., A Cationic Porphyrin, ZnPor, Disassembles *Pseudomonas aeruginosa* Biofilm Matrix, Kills Cells Directly, and Enhances Antibiotic Activity of Tobramycin, 2020.) This did not require known heme uptake systems or energy from the ETC. This finding led to testing whether other molecules, such as DNA or even whole phage, or phage genomic DNA can be transformed into PsA cells at sub-MIC levels of ZnPor.

Other molecules were tested using ZnPor (II) treated cells (at 4 µg/mL which is MIC). It was shown to be possible to "spoon feed" bacteria with molecules of interest, such as extant antibiotics, macromolecules (DNA and RNA), plasmids, even whole proteins, or bacteriophage. In this use of ZnPor (II), PsA cells were permeabilized at levels of ZnPor (II) that inhibit, but do not kill the cells. It was shown that the purified genomic DNA of the PEV2 phage entered cells treated with ZnPor (II) and productive phage were made (FIGS. 20A-20B and FIG. 21).

Example 5: Reducing Survival of Bacteria Resistant to Phage

Recently it has been reported that biofilm cells of PsA are capable of natural transformation by DNA. (Nolan L M, Turnbull L, Katrib M, Osvath S R, Losa D, Lazenby J J, Whitchurch C B. *Pseudomonas aeruginosa* is capable of natural transformation in biofilms, Microbiology (Reading). 2020 October; 166(10):995-1003. doi: 10.1099/mic.0.000956. PMID: 32749953; PMCID: PMC7660920. These results appear to confirm this as there are "rosettes of dead cells" in PsA biofilms exposed to the genomic DNA of the PEV2 (FIGS. 20A-20B). Notably, pre-treatment with ZnPor (II) led to far greater killing of biofilm cells. Since the ZnPor (II) was removed by thorough rinsing prior to the addition of the phage or phage DNA genome, the permeability was stable long enough for "transformation" of the cells with exogenous DNA. ZnPor (II) The PsA cells resumed growth after the removal of ZnPor (II). Being able to use phage genomes vs. whole phage bypassed the receptors on the outside of the cell, thus expanding the host range of phage. This was valuable in Phage Therapy as one of the limitations currently is that most phage are highly host specific. The ability to kill phage after they have killed the bacteria (using light activation) led to a "take no prisoners" approach and reduced the survival of bacteria resistant to the phage.

Example 6: CRISPR-Cas System

This ability of ZnPor (II), to create stable permeabilized bacterial cells made it possible to "transform" bacteria with DNA in situ in infections or in any natural setting (e.g., soil). Plasmids were delivered to bacterial cells that did not have a CRISPR-Cas system (e.g., CRISPR-Cas components have already been put into a plasmid). Since only about 50% of bacteria have a CRISPR-Cas system, ZnPor (II) provided a mechanism to study the addition of the system in these bacteria.

Example 7: ZnPor (II) as an Antimicrobial Agent with Killing Activity Against a Range of Microorganisms ZnPor (II) was a highly effective stand-alone anti-infective against planktonic and/or biofilm-associated bacterial cells. ZnPor (II) was effective at killing a wide range of bacteria with different cell wall/envelope construction e.g., Gram-negative (GN), Gram-positive (GP) bacteria as well as representative acid-fast microorganisms: *Pseudomonas aeruginosa* (GN), *S. aureus* MSSA and MRSA strains (GP); as well as *Listeria monocytogenes*, and *Mycobacterium smegmatis* (proxy for *M. tuberculosis*).

ZnPor (II) was effective at concentrations that were up to 100×lower than that which caused any toxicity of ex-vivo grown lung cells. It killed both Gram-negative (GN) and Gram-positive (GP) bacteria as well as Acid-fast bacteria: *Pseudomonas aeruginosa* (GN)-PA14 and PAO1; *Staphylococcus aureus*—MSSA and MRSA strains; as well as *Listeria monocytogenes*, and *Mycobacterium smegmatis* (proxy for *M. tuberculosis*). These bacteria represent some of the most difficult to treat and deadliest infections, in part due to the development of antibiotic resistance, even multi-drug resistant (MDR) strains.

ZnPor (II) exhibited anti-viral activity when tested with canonical bacteriophage and animal virus: Phage PEV2 and a Coronavirus isolated from a cold (ATCC). ZnPor (II) prevented viral infection. ZnPor (II) can interact with many macromolecules and may bind to important components of a virus, rendering it unable to infect cells. A number of studies have shown that light activation of select porphyrins is effective at killing animal viruses. This is due to the high levels of ROSs (Reactive Oxygen Species, e.g., superoxide) produced by activation of the porphyrin and which destroy a wide range of macromolecules (proteins, lipids etc.). In contrast, ZnPor (II) was able to inactivate viruses without light activation. ZnPor can bind to proteins, which may have accounted for how ZnPor (II) acted, in that it bound to the viral proteins such as the spike protein of Coronaviruses. If the Spike proteins bound to ZnPor (II) then the virus couldn't attach to the host cell binding receptor for the spike proteins. There are relatively few antiviral agents. While there are a number of porphyrins that can inactivate viruses using light activation, ZnPor (II) porphyrin has antiviral activity without light activation.

Example 8: Destruction of Bacteria and Bacterial Biofilms Formed on Surfaces

Studies with ZnPor (II) show bacterial biofilms were dissembled and can completely detach from a surface when ZnPor (II) was at higher concentrations. This is the first report of a small molecule that can dissemble the biofilm matrix and kill the encased bacteria. Biofilms can form at virtually any liquid/surface interface (fuel tanks, water pipes etc.), so the ability to dissemble biofilms has non-medical applications as well. Bacterial biofilms contain high levels of extracellular DNA secreted by the bacterium (Hynen, A L, et al., Multiple holins contribute to extracellular DNA release in *Pseudomonas aeruginosa* biofilms, 2021), which made them susceptible to agents that act on DNA. The biofilm matrices of bacterial pathogens were highly conserved in that they all contain eDNA. This translated into the wide application of ZnPor (II) against biofilms of different bacteria.

With respect to animate surfaces, bacterial biofilms formed on tissues and organs (e.g., CF lungs). Several bacterial pathogens are involved in the destruction of lung tissue of people with CF, as well as those suffering with diabetic foot ulcers and VAP, including *Pseudomonas aeruginosa* and *Staphylococcus aureus*. There is need to break up biofilms as they are considered the source of persistent infections associated with tissues such as the lungs of CF patients, burn wounds, diabetic foot ulcers and Ventilator associated pneumonia (VAP).

With respect to inanimate surfaces, bacterial biofilms readily form on inanimate surfaces: biomedical devices, titanium joints, catheters, Endotracheal tubes, and teeth. ZnPor (II) was an effective antimicrobial agent that exhibited-cidal (killing) activity at higher concentrations; while at lower concentrations ZnPor (II) acted as an agent to increase the efficacy of existing antibiotics/anti-infectives by making the biofilm porous. Bacteria growing in biofilms are up to 1000×more resistant to antibiotics than cells grown planktonically.

Example 9: ZnPor (II) can Kill Bacteria that are Inside Human Cells

A growing number of bacteria are being discovered as having the ability to enter and grow within human cells. The model bacterium used to test this was: *Listeria monocytogenes*. This bacterium is well known for its ability to survive inside human cells and using actin tails (sourced from the host cell) to propel themselves out of one cell and into another. The *L. monocytogenes* bacteria were incubated with macrophages. After being taken up, the macrophages were washed to get rid of any bacteria that did not get into the macrophages. Then macrophages were cracked open and plated on antibiotic plates to get a viable count of the number of cells taken up (control) and compared to macrophages treated with ZnPor (II). Treatment of the macrophages with ZnPor (II) resulted in a log reduction in the number of *Listeria* cells in the macrophages.

Other advantages which are obvious, and which are inherent to the invention, will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

REFERENCES

Yoho, J., C. Stroh, S. Swavey, and M. Kango-Singh. 2014. Toxicity and localization studies of a potential photodynamic therapy agent in Drosophila. Genesis 52(4):309 Photochem Photobiol Patel N, Swavey S, Robinson J. A Cationic Porphyrin, ZnPor, Disassembles *Pseudomonas aeruginosa* Biofilm Matrix, Kills Cells Directly, and Enhances Antibiotic Activity of Tobramycin. Antibiotics (Basel). 2020 Dec. 6; 9(12):875. doi: 10.3390/antibiotics9120875. PMID: 33291344; PMCID: PMC7762324.

Hynen A L, Lazenby J J, Savva G M, McCaughey L C, Turnbull L, Nolan L M, Whitchurch C B. Multiple holins contribute to extracellular DNA release in *Pseudomonas aeruginosa* biofilms. Microbiology (Reading), 2021 February; 167(2):000990. doi: 10.1099/mic.0.000990. PMID: 33400641; PMCID: PMC81311026.obiol. 2010 November; 61(5):411-6, doi: 10.1007/s00284-010-9629-y. Epub 2010 Apr. 6. PMID: 20372908.

Zemanick, E. T. and L. R. Hoffman, Cystic Fibrosis: Microbiology and Host Response. Pediatr Clin North Am, 2016. 63(4): p. 617-36.

Mogayzel, P. J., Jr., et al., *Cystic fibrosis pulmonary guidelines. Chronic medications for maintenance of lung health*. Am J Respir Crit Care Med, 2013. 187(7): p. 680-9.

Flume, P. A., et al., *Cystic fibrosis pulmonary guidelines: airway clearance therapies*. Respir Care, 2009. 54(4): p. 522-37.

Davis, P. B., M. Drumm, and M. W. Konstan, *Cystic fibrosis*. Am J Respir Crit Care Med, 1996. 154(5): p. 1229-56.

Simon, R. *Cystic fibrosis: Antibiotic therapy for chronic pulmonary infection*.

Rowbotham, New Jersey, et al., *The top 10 research priorities in cystic fibrosis developed by a partnership between people with CF and healthcare providers*. Thorax, 2018.

Mogayzel, P. J., Jr., et al., *Cystic Fibrosis Foundation pulmonary guideline. pharmacologic approaches to prevention and eradication of initial Pseudomonas aeruginosa infection*. Ann Am Thorac Soc, 2014.

Bjarnsholt, T., et al., *Pseudomonas aeruginosa biofilms in the respiratory tract of cystic fibrosis patients*. Pediatr Pulmonol, 2009. 44(6): p. 547-58.

Hoiby, N., O. Ciofu, and T. Bjarnsholt, *Pseudomonas aeruginosa biofilms in cystic fibrosis*. Future Microbiol, 2010. 5(11): p. 1663-74.

Murray, T. S., M. Egan, and B. I. Kazmierczak, *Pseudomonas aeruginosa chronic colonization in cystic fibrosis patients*. Curr Opin Pediatr, 2007. 19(1): p. 83-8.

Charnyi, A. M. and S. E. Krasovitskaia, [*Porphyrins*]. Usp Sovrem Biol, 1951. 32(2): p. 166-92.

Falk, J. E., *Porphyrins*. Br Med Bull, 1954. 10(3): p. 211-4.

Huang, H., et al., *Emerging applications of porphyrins in photomedicine*. Frontiers in Physics, 2015. 3(23).

Huang, X., K. Nakanishi, and N. Berova, *Porphyrins and metalloporphyrins: versatile circular dichroic reporter groups for structural studies*. Chirality, 2000. 12(4): p. 237-55.

Fiel R J, Howard J C, Mark E H, Datta Gupta. N. Interaction of DNA with a porphyrin ligand: evidence for intercalation. Nucleic Acids Res. 1979 Jul. 11; 6(9):3093-118. 10.1093/nar/6.9.3093. PMID: 573891; PMCID: PMC327919, Yoho, J. et al., Toxicity and localization studies of a potential photodynamic therapy agent in *Drosophila*, 2014.

Choi, J. K., A. D'Urso, and M. Balaz, *Chiroptical properties of anionic and cationic porphyrins and metalloporphyrins in complex with left-handed Z-DNA and right-handed B-DNA*. J Inorg Biochem, 2013. 127: p. 1-6.

Chiang, W.-C., et al., Extracellular DNA Shields against Aminoglycosides in <span class="named-content genus-species" id="named-content-1">*Pseudomonas aeruginosa*</span> Biofilms. Antimicrobial Agents and Chemotherapy, 2013. 57(5): p. 2352-2361.

Montanaro, L., et al., *Extracellular DNA in Biofilms*. The International Journal of Artificial Organs, 2011. 34(9): p. 824-831.

Okshevsky, M., V. R. Regina, and R. Meyer, *Extracellular DNA as a target for biofilm control*. Current Opinion in Biotechnology, 2015. 33: p. 73-80.

Munita, J. M. and C. A. Arias, *Mechanisms of Antibiotic Resistance*. Microbiology spectrum, 2016. 4(2): p. 10.1128/microbiolspec.VMBF-0016-2015.

Salcedo, D. E., et al., *The effects of antibiotics on the biofilm formation and antibiotic resistance gene transfer*. Desalination and Water Treatment, 2015. 54(13): p. 3582-3588.

Gula, G., et al., *Complex Signaling Networks Controlling Dynamic Molecular Changes in Pseudomonas aeruginosa Biofilm*. Curr Med Chem, 2019. 26(11): p. 1979-1993.

Vorkapic, D., K. Pressler, and S. Schild, *Multifaceted roles of extracellular DNA in bacterial physiology*. Curr Genet, 2016. 62(1): p. 71-9.

Collins, T. L., et al., *The effect of a cationic porphyrin on Pseudomonas aeruginosa biofilms*. Curr Microbiol, 2010. 61(5): p. 411-6.

Lutton, J. D., et al., *Zinc porphyrins: potent inhibitors of hematopoieses in animal and human bone marrow*. Proc Natl Acad Sci USA, 1997. 94(4): p. 1432-6.

Nolan L M, Turnbull L, Katrib M, Osvath S R, Losa. D, Lazenby J J, Whitchurch C B, Pseudomonas aeruginosa is capable of natural transformation in biofilms. Microbiology (Reading). 2020 October; 166(:995-1003. doi: 10.1099/mic.0.000956. PMID: 32749953; PMCID: PMC7660920.

Robinson, Jayne, et al. Combination therapy and methods for treating bacterial biofilms. 8,551,456. United States Patent and Trademark office. 8 Oct. 2013.

Robinson, Jayne, et al. Transition metal porphyrin complexes and methods of treatment using same. U.S. Pat. No. 9,364,537. United States Patent and Trademark Office. 14 Jun. 2016.

What is claimed is:

1. A method of inhibiting the growth of a virus comprising contacting the virus with zinc porphyrin (ZnPor (II)) in the absence of light activation.

2. The method of claim 1, wherein ZnPor is meso-5,10, 15-tris(N-methyl-4-pyridyl)-20-(pentafluorophenyl)porphyrinatozinc(II), tris-p-toluene sulfonate or meso-5,15-di(N-methyl-4-pyridyl)-10,20-di(pentafluorophenyl) porphyrinatozinc(II), di-p-toluene sulfonate.

3. The method of claim 1, further comprising enhancing the efficacy of the ZnPor using light activation from 380 nm to 700 nm.

4. The method of claim 3, wherein ZnPor (II) undergoes light activation with visible light having from 200W to 400W.

5. The method of claim 1, wherein treating the virus with ZnPor does not require oxygen and/or wherein the ZnPor is water soluble.

6. The method of claim 1, wherein the ZnPor is not toxic to a human lung cell or a human skin cell.

7. The method of claim 1, wherein the virus is a DNA virus.

8. The method of claim 1, wherein the virus being inhibited is present on an inanimate surface or has infected a subject.

9. The method of claim 1, wherein the virus is an RNA virus.

10. The method of claim 1, wherein inhibiting the virus comprises killing the virus.

11. The method of claim 1, wherein the virus is selected from the group consisting of: poxvirus, herpes virus, adenovirus, adeno-associated virus, lentivirus, retrovirus, rhabdovirus, papilloma virus, vesicular stomatitis virus, measles virus, Newcastle disease virus, picovirus Luna virus, Sindbis virus, papilloma virus, parvovirus, reovirus, coxsackie virus, influenza virus, mumps virus, poliovirus, Coronavirus, and Semliki Forest fever virus.

12. The method of claim 1, wherein the ZnPor is administered at a concentration less than a minimum inhibitory concentration (MIC).

13. The method of claim 1, wherein the method results in increasing the host range of a —bacteriophage, inactivating a —bacteriophage, and/or synergizing the ZnPor (II) with a bacteriophage to inhibit infection caused by a virus.

14. A method of treating or preventing biofilm formation of one or more microorganisms comprising contacting the biofilm with zinc porphyrin (ZnPor), wherein the biofilm is caused by a prokaryotic organism and/or a eukaryotic microorganism, wherein the biofilm is not caused by *Staphylococcus aureus*, *Staphylococcus aureus* MRSA and MSSA strains, *Pseudomonas aeruginosa*, *Pseudomonas aeruginosa* PA14, *Pseudomonas aeruginosa* PAO 1, or other *Pseudomonas* species.

15. The method of claim 14, wherein when biofilm is caused by a prokaryotic organism, the prokaryotic organism is selected from a group consisting of *Mycobacterium tuberculosis*, *Mycobacterium bovis*, *Mycobacterium bovis* strain BCG, BCG substrains, *Mycobacterium avium*, *Mycobacterium intracellular*, *Mycobacterium africanum*, *Mycobacterium kansasii*, *Mycobacterium marinum*, *Mycobacterium ulcerans*, *Mycobacterium smegmatis*, *Mycobacterium avium subspecies paratuberculosis*, *Nocardia asteroides*, other *Nocardia* species, *Legionella pneumophila*, other *Legionella* species, *Acetinobacter baumanii*, *Salmonella typhi*, *Salmonella enterica*, other *Salmonella* species, *Shigella boydii*, *Shigella dysenteriae*, *Shigella sonnei*, *Shigella flexneri*, other *Shigella* species, *Yersinia pestis*, *Pasteurella haemolytica*, *Pasteurella multocida*, other *Pasteurella* species, *Actinobacillus* pleuropneumonias, *Listeria monocytogenes*, *Listeria ivanovii*, *Bacillus subtilis*, *Brucella abortus*, other *Brucella* species, *Cowdria ruminantium*, *Borrelia burgdorferi*, *Bordetella avium*, *Bordetella pertussis*, *Bordetella bronchiseptica*, *Bordetella trematum*, *Bordetella hinzii*, *Bordetella pteri*, *Bordetella parapertussis*, *Bordetella ansorpii*, other *Bordetella* species, *Burkholderia mallei*, *Burkholderia psuedomallei*, *Burkholderia cepacian*, *Chlamydia pneumoniae*, *Chlamydia trachomatis*, *Chlamydia psittaci*, *Coxiella burnetii*, *Rickettsial species*, *Ehrlichia species*, *Staphylococcus epidermidis*, *Streptococcus mutans*, *Streptococcus pneumoniae*, *Streptococcus pyogenes*, *Streptococcus agalactiae*, *Escherichia coli*, *Vibrio cholerae*, *Campylobacter* species, *Neiserria meningitidis*, *Neiserria gonorrhea*, *Haemophilus influenzae*, *Haemophilus ducreyi*, other *Hemophilus* species, *Clostridium tetani*, other *Clostridium* species, *Yersinia enterolitica*, and other *Yersinia* species, wherein when the prokaryotic organism is a Gram positive organism, the Gram positive organism comprises, *Streptocuccus mutans*, or *Bacillus subtilis*; wherein when the biofilm is caused by a eukaryotic organism, the eukaryotic organism is selected from a group consisting of *Candida albicans*, *Cryptococcus neoformans*, *Histoplasma capsulatum*, *Aspergillus fumigatus*, *Coccidioides immitis*, *Paracoccidioides brasiliensis*, *Blastomyces dermitidis*, *Pneumocystis carnii*, *Penicillium marneffi*, or *Alternaria* alternatas.

16. The method of claim 14, wherein the ZnPor inhibits one or more virulence factors of the microorganism.

17. The method of claim 14, wherein the biofilm is present on an inanimate surface selected from the group consisting of: solid surfaces, biomedical devices, titanium joints, dental instruments, catheters, and Endotracheal tubes.

18. The method of claim 14, wherein the ZnPor is administered topically.

19. The method of claim 11, wherein the virus is a coronavirus.

20. The method claim 19, wherein the coronavirus is a Severe Acute Respiratory Syndrome (SARS) coronavirus (CoV).

21. A method of claim 20, wherein the SARS-CoV is SARS-CoV-2.

22. A method of claim 11, wherein the virus is a human immunodeficiency virus (HIV).

23. A method of claim 22, wherein the HIV is selected from the group consisting of: HIV1, and HIV2.

24. A method of claim 11, wherein the virus is selected from the group consisting of: Herpes Simplex virus- 1, Herpes Simplex virus-2, Varicella-Zoster virus, Epstein-Barr virus, Cytomegalovirus, Human Herpes virus-6, Variola virus, Vesicular stomatitis virus, Hepatitis A virus, Hepatitis B virus, Hepatitis C virus, Hepatitis D virus, Hepatitis E virus, Rhinovirus, Coronavirus (such as, for example, avian coronavirus (IBV), porcine epidemic diarrhea virus (PEDV), porcine respiratory coronavirus (PRCV), transmissible gastroenteritis virus (TGEV), feline coronavirus (FCoV), feline infectious peritonitis virus (FIPV), feline enteric coronavirus (FECV), canine coronavirus (CCoV), rabbit coronavirus (RaCoV), mouse hepatitis virus (MHV), rat coronavirus (RCoV), sialodacryadenitis virus of rats (SDAV), bovine coronavirus (BCoV), bovine enterovirus (BEV), porcine coronavirus HKU15 (PorCoV HKU15), Porcine epidemic diarrhea virus (PEDV), porcine hemagglutinating encephalomyelitis virus (HEV), turkey bluecomb coronavirus (TCoV), human coronavirus (HCoV)-229E, HCoV-0C43, HCoV-HKU1, HCoV-NL63, Severe Acute Respiratory Syndrome (SARS)-Coronavirus (CoV) (SARS-CoV), Severe Acute Respiratory Syndrome (SARS)-Coronavirus (CoV)-2 (SARS-CoV-2) (including, but not limited to the B1.351 variant, B.1.1.7 variant, USA-WA1/2020, or P.1 variant), or middle east respiratory syndrome (MERS) coronavirus (CoV) (MERS-CoV)), Influenza virus A, Influenza virus B, Measles virus, Polyomavirus, Human Papillomavirus, Respiratory syncytial virus, Adenovirus, Coxsackie virus, Dengue virus, Mumps virus, Poliovirus, Rabies virus, Rous sarcoma virus, Reovirus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Simian Immunodeficiency virus, Human T-cell Leukemia virus type-1, Hantavirus, Rubella virus, Simian Immunodeficiency virus, Human Immunodeficiency virus type-1, and Human Immunodeficiency virus type-2.

25. The method of claim 1, wherein the ZnPor is not bactericidal.

26. The method of claim 1, wherein inhibiting the microorganism comprises permeabilizing the microorganism.

27. The method of claim 1, wherein the ZnPor is administered at a concentration less than a minimum inhibitory concentration (MIC).

28. The method of claim 14, wherein the microorganism is permeabilized with DNA, a whole bacteriophage, a partial bacteriophage, an antibiotic, or any combination thereof.

29. The method of claim 28, wherein permeabilizing the microorganism comprises increasing the host range of the bacteriophage, inactivating the bacteriophage, and/or synergizing the ZnPor (II) with the bacteriophage to inhibit infection caused by the microorganism.

* * * * *